US010822419B2

United States Patent
Wang et al.

(10) Patent No.: US 10,822,419 B2
(45) Date of Patent: Nov. 3, 2020

(54) MASKING CHIMERIC ANTIGEN RECEPTOR T CELLS FOR TUMOR-SPECIFIC ACTIVATION

(71) Applicant: University of Southern California, Los Angeles, CA (US)

(72) Inventors: Pin Wang, Los Angeles, CA (US); Xiaolu Han, Los Angeles, CA (US); Paul Bryson, Culver City, CA (US)

(73) Assignee: University of Southern California, Los Angeles, CA (US)

( * ) Notice: Subject to any disclaimer, the term of this patent is extended or adjusted under 35 U.S.C. 154(b) by 172 days.

(21) Appl. No.: 15/574,743

(22) PCT Filed: Jun. 27, 2016

(86) PCT No.: PCT/US2016/039670
§ 371 (c)(1),
(2) Date: Nov. 16, 2017

(87) PCT Pub. No.: WO2016/210447
PCT Pub. Date: Dec. 29, 2016

(65) Prior Publication Data
US 2018/0148508 A1    May 31, 2018

Related U.S. Application Data

(60) Provisional application No. 62/185,398, filed on Jun. 26, 2015.

(51) Int. Cl.
| | | |
|---|---|---|
| C07K 16/28 | (2006.01) | |
| C07K 14/725 | (2006.01) | |
| C07K 14/705 | (2006.01) | |
| C07K 14/47 | (2006.01) | |
| C07K 7/00 | (2006.01) | |
| C07K 16/32 | (2006.01) | |
| A61P 35/00 | (2006.01) | |
| C07K 16/30 | (2006.01) | |
| A61K 38/00 | (2006.01) | |

(52) U.S. Cl.
CPC .......... *C07K 16/2863* (2013.01); *A61P 35/00* (2018.01); *C07K 7/00* (2013.01); *C07K 14/4748* (2013.01); *C07K 14/705* (2013.01); *C07K 14/7051* (2013.01); *C07K 14/70503* (2013.01); *C07K 14/70517* (2013.01); *C07K 14/70521* (2013.01); *C07K 14/70578* (2013.01); *C07K 16/28* (2013.01); *C07K 16/3015* (2013.01); *C07K 16/3023* (2013.01); *C07K 16/3038* (2013.01); *C07K 16/3053* (2013.01); *C07K 16/32* (2013.01); *A61K 38/00* (2013.01); *C07K 2317/24* (2013.01); *C07K 2317/56* (2013.01); *C07K 2317/622* (2013.01); *C07K 2317/70* (2013.01); *C07K 2317/73* (2013.01); *C07K 2317/76* (2013.01); *C07K 2319/02* (2013.01); *C07K 2319/03* (2013.01); *C07K 2319/50* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2013/0315906 A1* | 11/2013 | Lowman | C07K 16/2863 424/134.1 |
| 2014/0255313 A1 | 9/2014 | Vasiljeva et al. | |
| 2014/0322275 A1* | 10/2014 | Brogdon | A61K 38/00 424/277.1 |

FOREIGN PATENT DOCUMENTS

| | | | |
|---|---|---|---|
| CN | 103145849 A | 6/2013 | |
| CN | 107709356 A | 2/2018 | |
| JP | 2015-516813 A | 6/2015 | |
| JP | 2018-518972 A | 7/2018 | |
| WO | 2013/123061 A1 | 8/2013 | |
| WO | 2014/134165 A1 | 9/2014 | |
| WO | WO-2014197612 A1 * | 12/2014 | .............. A61P 29/00 |
| WO | 2016/210447 A1 | 12/2016 | |

OTHER PUBLICATIONS

Gura (Science, 1997, 278:1041-1042) (Year: 1997).*
Kaiser (Science, 2006, 313:1370) (Year: 2006).*
Patel et al. (Anticancer Res. 2007: 3355-3366) (Year: 2007).*
Jena et al. (Blood Aug. 19, 2010 116(7): 1035-1044) (Year: 2010).*
Almagro & Fransson, (Frontiers in Bioscience 2008; 13:1619-33) (Year: 2008).*
Extended European Search Report for EP 16815514.1, dated Oct. 25, 2018, 7 Pages.
Desnoyers et al., Tumor-Specific Activation of an EGFR-Targeting Probody Enhances Therapeutic Index, Science Translation Medicine, 2013, vol. 5(207), 207ra144, 12 Pages.
Federov et al., PD-1- and CTLA-4-Based Inhibitory Chimeric Antigen Receptors (iCARs) Divert Off-Target Immunotherapy Responses, 2013, Science Translation Medicine, vol. 5(215), 215ra172, 14 Pages.
Han et al., Masked Chimeric Antigen Receptor for Tumor-Specific Activation, 2017 Molecular Therapy, vol. 25(1), Pages 274-284.
International Search Report and Written Opinion for PCT/US2016/039670 dated Oct. 4, 2016, 11 pages.
Jiang et al., A Novel Peptide Isolated from a Phage Display Peptide Library with Trastuzumab Can Mimic Antigen Epitope of HER-2, 2005, J. Biol. Chem., vol. 280(6), pp. 4656-4662.

(Continued)

*Primary Examiner* — Peter J Reddig
(74) *Attorney, Agent, or Firm* — Nixon Peabody LLP

(57) ABSTRACT

The invention is directed to a masked chimeric antigen receptor, comprising: (a) a masking peptide; (b) one or more antigen-specific targeting domains; (c) an extracellular spacer domain; (d) a transmembrane domain; (e) at least one co-stimulatory domain; and (f) an intracellular signaling domain. The mCARs are activated upon cleavage of the masking peptide.

20 Claims, 12 Drawing Sheets

Specification includes a Sequence Listing.

(56) References Cited

OTHER PUBLICATIONS

Rice et al., Bacterial Display using Circularly Permuted Outer Membrane Protein OmpX Yields High Affinity Peptide Ligands, 2006, Protein Science, vol. 15, pp. 825-836.
Zhao et al., A Herceptin-Based Chimeric Antigen Receptor with Modified Signaling Domains Leads to Enhanced Survival of Transduced T Lymphocytes and Antitumor Activity, 2009, The Journal of Immunology, vol. 183, pp. 5563-5574.
Caruso et al., EGFR-mediated Lysis of Glioma Cell Lines by Genetically Modified T Cells, Journal of Immunotherapy, Abstracts for the 26th Annual Scientific Meeting of the Society for Immunotherapy of Cancer (SITC), 2011, vol. 34(9), p. 674.
Neoplasia.com, Cellular Immunotherapy for Carcinoma Using Genetically Modified EGFR-Specific T Lymphocytes, Neoplasia, 2013, vol. 15, No. 5, p. 544-553.
CN 201680037492.9 Office Action dated Aug. 5, 2020, 22 pages.

\* cited by examiner

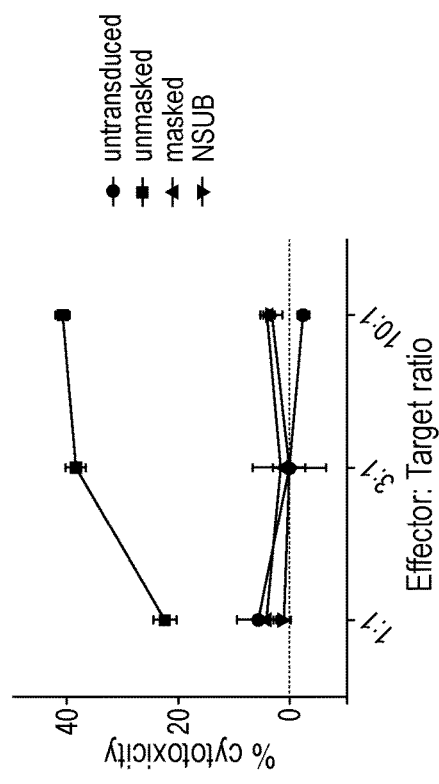
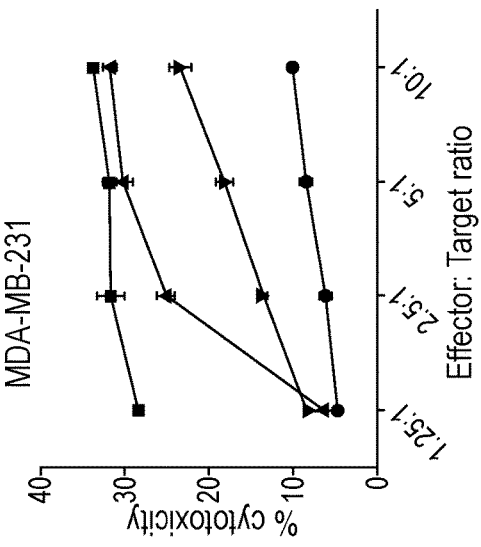
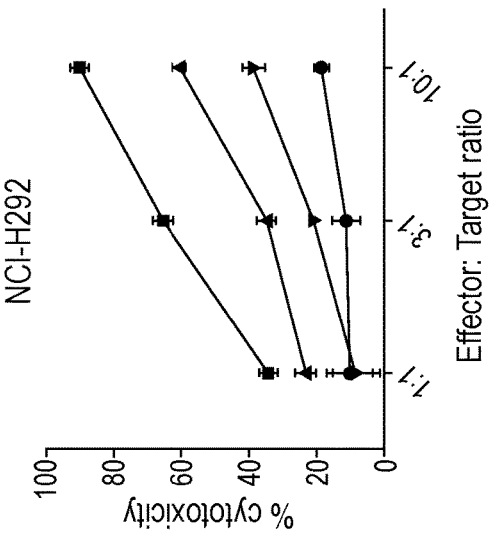

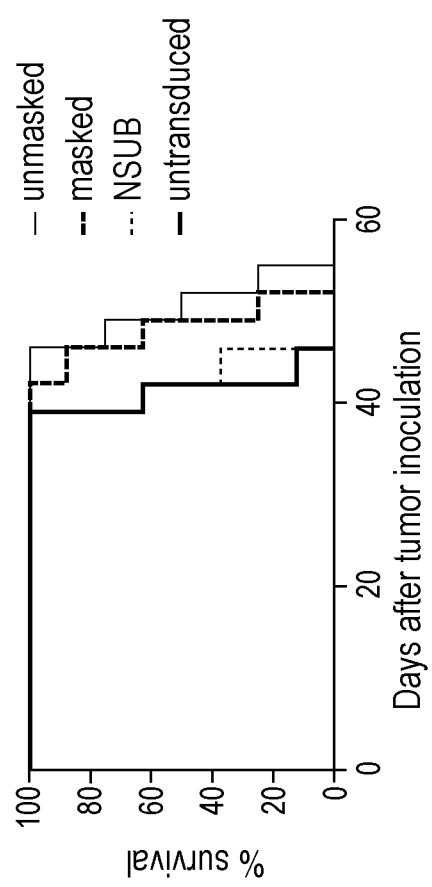
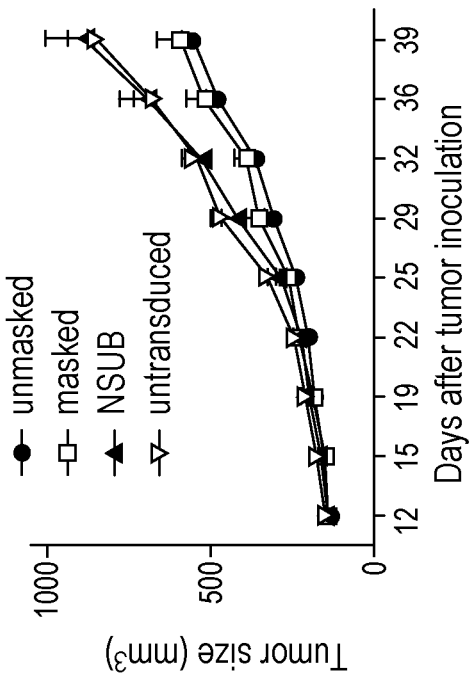
FIG. 10A
FIG. 10C
FIG. 10B

MASKING CHIMERIC ANTIGEN RECEPTOR T CELLS FOR TUMOR-SPECIFIC ACTIVATION

CROSS-REFERENCE TO RELATED APPLICATIONS

This application is a National Phase of International Application No. PCT/US2016/039670 filed Jun. 27, 2016, which designated the U.S. and that International Application was published under PCT Article 21(2) in English, which also includes a claim of priority under 35 U.S.C. § 119(e) to U.S. provisional patent application No. 62/185,398 filed Jun. 26, 2015, the entirety of which is hereby incorporated by reference.

STATEMENT REGARDING FEDERALLY SPONSORED RESEARCH OR DEVELOPMENT

This invention was made with government support under Grants No. CA170820, EB017206, and CA132681, awarded by the National Institute of Health. The government has certain rights in the invention.

REFERENCE TO SEQUENCE LISTING

The Sequence Listing submitted Sep. 25, 2019, as a text file named "SequenceListing-065715-000066US00_ST25" created on Aug. 13, 2019 and having a size of 16,384 bytes, is hereby incorporated by reference.

FIELD OF INVENTION

The invention relates to activatable chimeric antigen receptors and to genetically engineered cells using the same. The activatable mCARs are inactive when masked and active when unmasked.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Adoptive transfer of T cells, especially chimeric antigen receptor (CAR)-engineered T cells, has emerged as a promising approach in cancer immunotherapy. CARs are synthetic receptors composed of an extracellular single-chain variable fragment (scFv) that specifically recognizes tumor-associated antigens (TAAs), a hinge, a transmembrane domain, and intracellular signaling and costimulatory domains. Unlike naturally occurring T cell receptors, CARs can directly recognize their target antigens without restrictions imposed by major histocompatibility complex (MHC) molecules and can potentially mediate high levels of cell-killing activity.

CAR-modified T cell (CAR-T) therapy has shown remarkable success in multiple clinical trials for treating B cell malignancies through targeting the B cell-specific receptor CD19. This has sparked significant interest in extending the CAR-T technology for treatment of solid tumors, and several ongoing clinical trials are aimed at testing such treatment modalities. However, one challenging aspect of this transition is the identification of ideal solid tumor antigens that are restricted to tumor cells. Although numerous solid tumor antigens have been identified, most of them are also expressed at low levels in normal tissues. It is this low level of antigen expression in healthy cells that could result in activating CAR-T cells and lead to "on-target off-tumor" toxicity. For example, infusion of human epidermal growth factor receptor 2 (HER2)-specific CAR-T cells in one patient caused lethal inflammatory cytokine release due to expression of HER2 in lung tissues. Considering the challenge of identifying ideal tumor antigens, one strategy to ameliorate the undesired on-target but off-tumor effect is to engineer tumor-selectivity mechanisms into the CAR structure to allow better differentiation between target antigens in the tumor microenvironment and those in normal tissues.

T cell immunotherapy is a powerful treatment that can lead to long term cures in patients with melanoma, B cell lymphomas, and other cancers. One common method is to genetically engineer T cells ex vivo to express chimeric antigen receptors (CARs), which can recognize target antigens without the need for MHC presentation. These CAR-T cells have the potential to generate very high levels of anti-tumor activity, but they may also display increased off-target cell killing. Therefore there is a need in the art to minimize such side-effect. Described herein are compositions that reduce the off-target cell killing of CAR-T cells.

SUMMARY OF THE INVENTION

The following embodiments and aspects thereof are described and illustrated in conjunction with systems, compositions and methods which are meant to be exemplary and illustrative, not limiting in scope.

T cells expressing chimeric antigen receptors have the potential to generate very high levels of anti-tumor activity, but they may also display increased off-target cell killing. To minimize such side effects, we have designed a chimeric antigen receptor (CAR) that contains an N-terminal masking peptide that blocks the ability of the CAR to bind to its target, epidermal growth factor receptor (EGFR), a tumor associated antigen highly expressed in a wide variety of tumors. The masking peptide can be cleaved by, for example, proteases commonly active in the tumor microenvironment, thus enabling the mCAR to only recognize their target antigen at the tumor site.

Provided herein are compositions comprising masked chimeric antigen receptors (mCARs) wherein the CARs are inactive when masked and active when the mask is cleaved. In an embodiment, the mCAR comprises, consists of or essentially consists of the sequence shown in Table 1 and/or SEQ ID NO: 29. As described herein, the masking peptide comprises a mask which prevents premature binding of the antigen-specific targeting domain in the mCAR to its target, a cleavage site which may be a substrate of proteases, a linker sequence that connects the mask to the cleavage site and a linker sequence that links the cleavage site to the car.

In an embodiment, the structural arrangement of the mCAR from N-terminus to C-terminus, when the mask is not cleaved, is mask-linker-cleavage site-linker-CAR. In an embodiment, the structural arrangement of the mCAR from N-terminus to C-terminus, when the mask is cleaved, is linker-CAR.

In an embodiment, the structural arrangement of the mCAR from N-terminus to C-terminus, when the mask is not cleaved, comprises, consists of or essentially consists of mask-linker-cleavage site-linker-antigen specific targeting domain-transmembrane domain-costimulatory domain-intracellular signaling domain. Additional sequences may be present between each domain to, for example, provide further flexibility and stability to the mCAR.

In an embodiment, the structural arrangement of the mCAR from N-terminus to C-terminus, when the mask is not cleaved, comprises, consists of or essentially consists of mask-linker-cleavage site-linker-antigen specific targeting domain-extracellular spacer domain-transmembrane domain-costimulatory domain-intracellular signaling domain. Additional sequences may be present between each domain to, for example, provide further flexibility and stability to the mCAR.

In an embodiment, the mCAR that is specific for EGFR comprises a masking peptide wherein the mask in the masking peptide comprises, consist of or consists essentially of a sequence that is at least 100%, 99%, 98%, 97%, 96% 95%, 94%, 93%, 92%, 91%, 90%, 85% or 80% identical to CISPRGCPDGPYVMY (SEQ ID NO:1). In another embodiment, the mCAR that is specific for Her2 comprises a masking peptide wherein the mask in the masking peptide comprises, consist of or consists essentially of a sequence that is at least 100%, 99%, 98%, 97%, 96% 95%, 94%, 93%, 92%, 91%, 90%, 85% or 80% identical to LLGPYEL-WELSH (SEQ ID NO: 17). In further embodiments, the mCAR that is specific for GD2 ganglioside comprises a masking peptide wherein the mask in the masking peptide comprises or consists of or consists essentially of the sequence that is at least 100%, 99%, 98%, 97%, 96% 95%, 94%, 93%, 92%, 91%, 90%, 85% or 80% identical to RCNPMEPPRCWAAEGD (SEQ ID NO: 22) or that is at least 100%, 99%, 98%, 97%, 96% 95%, 94%, 93%, 92%, 91%, 90%, 85% or 80% identical to (VCNPLTGALLC-SAAEGD) (SEQ ID NO: 23). In additional embodiments, the mCAR that is specific for carbonic anhydrase 9 (CA-IX) comprises a masking peptide wherein the mask in the masking peptide comprises or consists of or consists essentially of the sequence that is at least 100%, 99%, 98%, 97%, 96% 95%, 94%, 93%, 92%, 91%, 90%, 85% or 80% identical to LSTAFARV (SEQ ID NO: 24) or that is at least 100%, 99%, 98%, 97%, 96% 95%, 94%, 93%, 92%, 91%, 90%, 85% or 80% identical to ALGPGREYRAL (SEQ ID NO: 25).

In an embodiment, the mCAR comprises a masking peptide wherein the cleavage site in the masking peptide comprises, consist of or essentially consists of a sequence that is at least 100%, 99%, 98%, 97%, 96% 95%, 94%, 93%, 92%, 91%, 90%, 85% or 80% identical to LSGRSDNH (SEQ ID NO: 2).

In an embodiment, the mCAR comprises an antigen-specific targeting domain which specifically binds and inhibits to (EGFR). In an embodiment, the EGFR inhibitor comprises, consists of or essentially consists of the variable light chain sequence that is at least 100%, 99%, 98%, 97%, 96% 95%, 94%, 93%, 92%, 91%, 90%, 85% or 80% identical to QILLTQSPVILSVSPGERVSFSCRASQSIGT-NIHWYQQRTNGSPRLLIKYASESISGIPSR FSGSGS-GTDFTLSINSVESEDIADYYCQQNNNWPTTFGAGT-KLELKR (SEQ ID NO: 3) and a variable heavy chain sequence that is at least 100%, 99%, 98%, 97%, 96% 95%, 94%, 93%, 92%, 91%, 90%, 85% or 80% identical to QVQLKQSGPGLVQPSQSLSITCTVSGFSLTNYGVH-WVRQSPGKGLEWLGVIWSGGN TDYNTPFTSRL-SINKDNSKSQVFFKMNSLQSNDTAIYYCARALTYY-DYEFAYWGQG TLVTVSS (SEQ ID NO: 4).

In some embodiments, the mCAR comprises, consists of or essentially consists of sequence that is at least 100%, 99%, 98%, 97%, 96% 95%, 94%, 93%, 92%, 91%, 90%, 85% or 80% identical to the sequences shown in Table 1 and/or SEQ ID NO: 29.

Also provided herein are methods for producing a quantity of T-cells expressing a masked chimeric antigen receptor. The methods include transfecting T-cells with vectors encoding masked chimeric antigen receptors described herein and stimulating the one or more T cells with cells expressing antigens targeted by the antigen-specific targeting domain or with recombinant antigen specific to the ASTD of the mCAR or a combination thereof. In some embodiments, stimulation of the transfected cells results in T-cell proliferation so as to produce a quantity of T-cells.

Also provided herein are methods for treating, inhibiting, reducing the symptoms of or delaying/reducing the progression of a disease in a subject. The methods include administering to the subject an effective amount of a composition comprising mCARs described herein. In an embodiment, the mCAR in the composition comprises the sequence shown in Table 1 and/or SEQ ID NO: 29. In an embodiment, the mCAR specifically binds EGFR. In an embodiment, the disease is any disease treatable by inhibiting EGFR. In an embodiment, the disease is cancer. In some embodiments, the cancer is any one or more of lung cancer, colorectal cancer, breast cancer, head and neck cancer, melanoma, glioblastoma, pancreatic cancer, ovarian cancer. In an embodiment, the mCAR specifically binds GD2 ganglioside and the cancer is neuroblastoma, melanoma, small cell lung cancer, osteosarcoma or soft tissue sarcomas. In one embodiment, the mCAR specifically binds GD2 ganglioside and the cancer is neuroblastoma. In a further embodiment, the mCAR specifically binds carbonic anhydrase 9 and the cancer is renal cell carcinoma, superficial bladder cancer or infiltrating urothelial carcinoma. In one embodiment, the mCAR specifically binds carbonic anhydrase 9 and the cancer is renal cell carcinoma.

Also provided herein are methods for treating, inhibiting, reducing the symptoms of or delaying/reducing the progression of lung cancer in a subject. The methods include administering to the subject an effective amount of a composition comprising mCARs described herein. In an embodiment, the mCAR in the composition comprises, consists of or consists essentially of the sequence shown in Table 1 and/or SEQ ID NO: 29. In an embodiment, the mCAR specifically binds EGFR.

BRIEF DESCRIPTION OF FIGURES

(FIG. 1A) Schematic of the rationale design of masked CAR to improve tumor selectivity. In the tumor microenvironment with the presence of proteases, the masking peptide is cleaved and the previously blocked antigen-binding site of the single chain variable fragment (scFv) is exposed. (FIG. 1B) Schematic representation of various anti-EGFR mCAR constructs. The scFv sequence was derived from the monoclonal antibody cetuximab. The scFv was fused in frame with the CD8a hinge and transmembrane domain, followed by the CD28/41BB/CD3t signaling domains, and then cloned into the retroviral vector to yield the unmasked CAR. The masking peptide and protease-sensitive linker were inserted upstream of scFv in the unmasked CAR to generate masked mCAR construct. The masking peptide and noncleavable GS linker were inserted upstream of scFv in the unmasked CAR to yield the NSUB (No protease SUBstrate sequence) CAR construct.

(FIG. 6A) The three groups of CAR-T cells were stained with biotinylated protein L followed by APC-conjugated streptavidin to detect CAR expression on the cell surface. (FIG. 6B) CAR-T cells were incubated with recombinant human EGFR-Fc protein followed by staining with PE-conjugated goat anti-human Fc antibody to assess the binding capability of CARs to their target antigen, human EGFR.

(FIG. 8A) On day 10 after activation and expansion ex vivo, unmasked, masked and NSUB CAR-T cells were cocultured with K562, K562-EGFR, MDA-MB-231 or NCI-H292 cells with GolgiPlug inhibitors for 6 hours. Unstimulated CAR-T cells were used as negative controls, whereas CAR-T cells stimulated with anti-CD3/CD28 antibodies were used as positive controls. Interferon gamma (IFN-γ) production was measured by intracellular staining. $CD8^+$ T cells were shown in each panel. IFN-γ-secreting CD8 T cells were gated, and their percentage over total $CD8^+$ T cells is shown in each scatter plot. (FIG. 8B) The summarized statistics were shown in bar graphs (n=3, mean±SEM; ns, not significant; *, P<0.05; , P<0.01; *, P<0.001, one-way ANOVA with Tukey's multiple comparison).

FIG. 9A-FIG. 9C depicts, in accordance with an embodiment of the invention, cytotoxicity of various CAR-T cells against different target cell lines in vitro. The unmasked, masked and NSUB CAR-T cells were cocultured with different target cell lines. (FIG. 9A) CAR-T cells were cocultured for 4 hours with K562-EGFR cells at 1:1, 3:1 or 10:1 effector-to-target ratios and cytotoxicity against K562-EGFR was measured and shown in the figure. (FIG. 9B) CAR-T cells were cocultured for 18 hours with NCI-H292 cells at 1:1, 3:1 or 10:1 effector-to-target ratios and cytotoxicity was measured. (FIG. 9C) CAR-T cells were cocultured for 18 hours with MDA-MB-231 cells at 1:1, 2.5:1, 5:1 or 10:1 effector-to-target ratios, and cytotoxicity was measured.

FIG. 10A-FIG. 10C depicts, in accordance with an embodiment of the invention, Antitumor efficacy of CAR-T cells in human lung cancer xenograft model. (FIG. 10A) Schematic representation of the in vivo CAR-T treatment protocol. NCI-H292 cells were injected into the right flank of NSG mice on day 0. Mice were randomized into 4 groups (n=8 each group) and treated with 4 million unmasked, masked, or NSUB CAR-T cells on day 13 and day 26; untransduced T cells were included as controls. Tumor size was measured by caliper twice every week. (FIG. 10B) Tumor growth curve in each group was shown as mean±SEM (ns, not significant; *, P<0.05; **, P<0.01). (FIG. 10C) Mouse survival curve was calculated using the Kaplan-Meier method.

DETAILED DESCRIPTION OF THE INVENTION

Figure 1A:
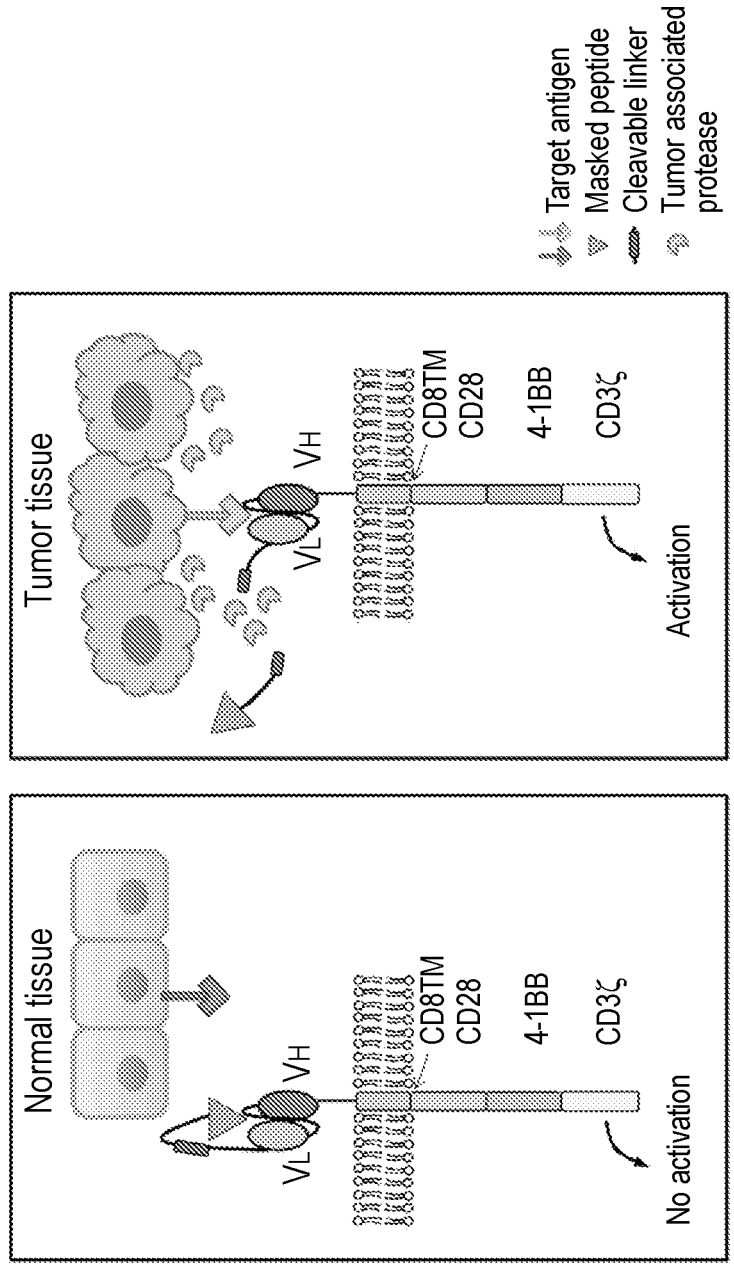
FIG. 1A-FIG. 1B depicts, in accordance with an embodiment of the invention, a schematic representations of unmasked, masked, and NSUB forms of anti-EGFR CAR constructs.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The invention described herein provides chimeric antigen receptors (CARs) which are activatable or masked (mCARs). Chimeric antigen receptors are engineered receptors which graft an immune specificity onto a genetically engineered cell. The masking peptides are unique to each antigen binding site on the CAR and render the CAR inactive until activated, for example by cleaving the linker that joins the CAR to the masking peptide.

"Masking peptide" (MP) as used herein refers to a peptide that inhibits the binding of the ASTD of the CAR to the antigen on the target cell when the MP is in an uncleaved state. The MP is linked to the CAR via a cleavable linker moiety. The MP comprises a mask (peptide) which prevents the CAR from binding the antigen on the target cell and cleavage site. In some embodiments, a linker sequences separates the masking peptide and the cleavage site and the masking peptide (MP) has the structure mask-linker-cleavage site. The cleavage site includes amino acids which are recognized by proteases. The mask may be 5-50 amino acids longs. In a cleaved state, the MP does not interfere with the binding of the CAR to the antigen on the target cell. In some embodiments, the structural arrangement of the masked CAR (mCAR) in the uncleaved state from N-terminus to C-terminus is MP-L-ASTD-ESD-TM-CSD-ISD. In some embodiments, the structural arrangement of the mCAR in the uncleaved state from N-terminus to C-terminus is MP-L-ASTD-TM-CSD-ISD. In various embodiments, the masking peptide is unique to each ASTD.

"Antigen-specific targeting domain" (ASTD) as used herein refers to the domain/region of the CAR which targets specific antigens. The mCARs may comprise one or more ASTDs. The ASTDs are extracellular and may comprise an antibody or a functional equivalent thereof or a fragment thereof or a derivative thereof. The targeting domain/regions may comprise full length heavy chain, Fab fragments, single chain Fv (scFv) fragments, divalent single chain antibodies or diabodies, each of which are specific to the target antigen. As will be appreciated by those of skill in the art, in some embodiments, any molecule that binds a given antigen with high affinity can be used as an ASTD, for example, linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response.

"Chimeric antigen receptor" or "CAR" or "CARs" as used herein refers to engineered receptors, which graft an antigen specificity onto cells (for example T cells such as naïve T cells, central memory T cells, effector memory T cells or combination thereof). CARs are also known as artificial T-cell receptors, chimeric T-cell receptors or chimeric immunoreceptors. The CARs comprise one or more antigen-specific targeting domains, an extracellular domain, a transmembrane domain, one or more co-stimulatory domains, and an intracellular signaling domain. In one embodiment, if the CAR targets two different antigens, the antigen-specific targeting domains may be arranged in tandem and separated by linker sequences.

"Co-stimulatory domain" (CSD) as used herein refers to the portion of the CAR which enhances the proliferation, survival and/or development of memory cells. The CARs may comprise one or more co-stimulatory domains. Each co-stimulatory domain comprises the costimulatory domain of any one or more of, for example, members of the TNFR superfamily, CD28, CD137 (4-1BB), CD134 (OX40), Dap10, CD27, CD2, CD5, ICAM-1, LFA-1(CD11a/CD18), Lck, TNFR-I, TNFR-II, Fas, CD30, CD40 or combinations thereof. Other co-stimulatory domains (e.g., from other proteins) will be apparent to those of skill in the art and may be used in connection with alternate embodiments of the invention.

"Extracellular spacer domain" (ESD) as used herein refers to the hydrophilic region which is between the antigen-specific targeting domain and the transmembrane domain. In some embodiments, the mCARs of the invention may or may not include an extracellular spacer domain. The extracellular spacer domains include but are not limited to Fc fragments of antibodies or fragments or derivatives thereof, hinge regions of antibodies or fragments or derivatives thereof, CH2 regions of antibodies, CH3 regions of antibodies, artificial spacer sequences or combinations thereof.

"Intracellular signaling domain" (ISD) or "cytoplasmic domain" as used herein refer to the portion of the CAR which transduces the effector function signal and directs the cell to perform its specialized function. Examples of domains that transduce the effector function signal include but are not limited to the $\zeta$ chain of the T-cell receptor complex or any of its homologs (e.g., $\eta$ chain, Fc$\epsilon$R1$\gamma$ and $\beta$ chains, MB1 (Ig$\alpha$) chain, B29 (Ig$\beta$) chain, etc.), human CD3 zeta chain, CD3 polypeptides ($\Delta$, $\delta$ and $\epsilon$), syk family tyrosine kinases (Syk, ZAP 70, etc.), src family tyrosine kinases (Lck, Fyn, Lyn, etc.) and other molecules involved in T-cell transduction, such as CD2, CD5 and CD28.

"Linker" (L) or "linker domain" or "linker region" as used herein refer to an oligo- or polypeptide region from about 1 to 100 amino acids in length, which links together any of the domains/regions of the CAR and links the CAR to the masking peptide. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. In some embodiments, the cleavable link the masking peptide to the CAR. Examples of cleavable linkers include 2A linkers (for example T2A), 2A-like linkers or functional equivalents thereof and combinations thereof. In some embodiments, the linkers include the picornaviral 2A-like linker, CHYSEL (SEQ ID NO: 5) sequences of porcine teschovirus (P2A), *Thosea asigna* virus (T2A) or combinations, variants and functional equivalents thereof. In other embodiments, the linker sequences may comprise Asp-Val/Ile-Glu-X-Asn-Pro-Gly$^{(2A)}$-Pro$^{(2B)}$ motif (SEQ ID NO: 6 and SEQ ID NO: 7), which results in cleavage between the 2A glycine and the 2B proline. Other linkers will be apparent to those of skill in the art and may be used in connection with alternate embodiments of the invention.

"Transmembrane domain" (TMD) as used herein refers to the region of the CAR which crosses the plasma membrane. The transmembrane domain of the CAR of the invention is the transmembrane region of a transmembrane protein (for example Type I transmembrane proteins), an artificial hydrophobic sequence or a combination thereof.

"B-cell associated diseases" as used herein include B-cell immunodeficiencies, autoimmune diseases and/or excessive/uncontrolled cell proliferation associated with B-cells (including lymphomas and/or leukemias). Examples of such diseases, wherein mCARs of the invention may be used for therapeutic approaches include but are not limited to systemic lupus erythematosus (SLE), diabetes, rheumatoid arthritis (RA), reactive arthritis, multiple sclerosis (MS), pemphigus vulgaris, celiac disease, Crohn's disease, inflammatory bowel disease, ulcerative colitis, autoimmune thyroid disease, X-linked agammaglobulinaemia, pre-B acute lymphoblastic leukemia, systemic lupus erythematosus, common variable immunodeficiency, chronic lymphocytic leukemia, diseases associated with selective IgA deficiency and/or IgG subclass deficiency, B lineage lymphomas (Hodgkin's lymphoma and/or non-Hodgkin's lymphoma), immunodeficiency with thymoma, transient hypogammaglobulinaemia and/or hyper IgM syndrome, as well as virally-mediated B-cell diseases such as EBV mediated lymphoproliferative disease, and chronic infections in which B-cells participate in the pathophysiology.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Conditions", "disease conditions," "diseases" and "disease state" as used herein include physiological states in which diseased cells may be targeted with the CARs of the invention, expressing, for example, antibodies against specific antigens on the diseased cells. Examples of antigens which may be targeted include but are not limited to antigens expressed on B-cells, antigens expressed on carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases. In an exemplary embodiment, the antigen targeted is EGFR.

"Effector function" refers to the specialized function of a differentiated cell. Effector function of a T-cell, for example, may be cytolytic activity or helper activity including the secretion of cytokines.

"Genetically modified cells", "redirected cells", "genetically engineered cells" or "modified cells" as used herein refer to cells that express the mCAR of the invention. The genetically modified cells include but are not limited to genetically modified T-cells, NK cells, hematopoietic stem cells, pluripotent embryonic stem cells or embryonic stem cells. The genetically modified cells express the mCARs of the invention, which mCARs are activatable and may target any of the antigens expressed on the surface of target cells "Immune cell" as used herein refers to the cells of the mammalian immune system including but not limited to antigen presenting cells, B-cells, basophils, cytotoxic T-cells, dendritic cells, eosinophils, granulocytes, helper T-cells, leukocytes, lymphocytes, macrophages, mast cells, memory cells, monocytes, natural killer cells, neutrophils, phagocytes, plasma cells and T-cells.

"Immune response" as used herein refers to immunities including but not limited to innate immunity, humoral immunity, cellular immunity, immunity, inflammatory response, acquired (adaptive) immunity, autoimmunity and/or overactive immunity.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

"Naked DNA" as used herein refers to DNA encoding a CAR cloned in a suitable expression vector in proper orientation for expression. Viral vectors which may be used include but are not limited SIN lentiviral vectors, retroviral vectors, foamy virus vectors, adeno-associated virus (AAV) vectors, hybrid vectors and/or plasmid transposons (for example sleeping beauty transposon system) or integrase based vector systems. Other vectors that may be used in connection with alternate embodiments of the invention will be apparent to those of skill in the art.

"Single chain variable fragment", "single-chain antibody variable fragments" or "scFv" antibodies as used herein refer to forms of antibodies comprising the variable regions of only the heavy and light chains, connected by a linker peptide.

"Target cell" as used herein refers to cells which are involved in a disease and can be targeted by the genetically modified cells of the invention (including but not limited to genetically modified T-cells, NK cells, hematopoietic stem cells, pluripotent stem cells, and embryonic stem cells). Other target cells will be apparent to those of skill in the art and may be used in connection with alternate embodiments of the invention.

The terms "T-cell" and "T-lymphocyte" are interchangeable and used synonymously herein. Examples include but are not limited to naïve T cells, central memory T cells, effector memory T cells or combinations thereof.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

"Transduction" as used herein refers to the introduction of a foreign nucleic acid into a cell using a viral vector.

"Transfection" as used herein refers to the introduction of a foreign nucleic acid into a cell using recombinant DNA technology. The term "transformation" means the introduction of a "foreign" (i.e. extrinsic or extracellular) gene, DNA or RNA sequence to a host cell, so that the host cell will express the introduced gene or sequence to produce a desired substance, such as a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Tumor," as used herein refers to all neoplastic cell growth and proliferation, whether malignant or benign, and all pre-cancerous and cancerous cells and tissues.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

T cells expressing chimeric antigen receptors have the potential to generate very high levels of anti-tumor activity, but they may also display increased off-target cell killing. To minimize such side effects, the inventors describe CARs with N-terminal masking peptide that blocks the ability of the CAR to bind to its target prematurely.

Described herein are masked/activatable chimeric antigen receptors (mCARs) which comprise a chimeric antigen receptor specific to one or more antigens and a masking peptide. The masking peptide blocks the premature binding of the antigen-specific binding region on the CAR to the antigen on the target cell. In general embodiments, the present invention relates to mCARs, nucleic acid sequences encoding the mCARs, the vectors comprising the nucleic acids encoding the mCARs, viruses comprising the nucleic acid sequences encoding the mCARs, host cells (such as genetically modified cells) expressing the mCARs and using the mCARs as therapeutic agents. The mCARs of the invention are constructed so that they may be expressed in cells, which in turn proliferate in response to the presence of at least one molecule that interacts with at least one antigen-specific targeting domain, for instance, an antigen. Specifically, the interaction between the antigen and the antigen-binding domain promotes proliferation of cells expressing the mCARs. Other factors (e.g. cytokines in the microenvironment, affinity of the binding, presence of regulatory cells, etc.), may also promotes proliferation of cells expressing the mCARs.

The mCARs described herein may be synthesized as single polypeptide chains and comprises a masking peptide, one or more antigen-specific targeting domains, an extracellular spacer domain, a transmembrane domain, one or more co-stimulatory domains and an intracellular signaling domain. In this embodiment, the masking peptide is at the N-terminus of the antigen-specific targeting domains and is arranged in tandem and separated by a linker peptide. The antigen-specific targeting domain is linked to an extracellular spacer domain which is linked to the transmembrane domain. The transmembrane domain is linked to the co-stimulatory domain. The co-stimulatory domain is linked to the intracellular signaling domain which is at the C-terminus. If more than one co-stimulatory domain is used, the multiple co-stimulatory domains may be arranged in tandem with the transmembrane domain at its N-terminus and the intracellular signaling domain at its C-terminus. Polynucleotides encoding these polypeptides may further comprise an N-terminal signal sequence which directs the mCAR to the cell surface as a type I transmembrane protein. The antigen-specific targeting domain may be extracellular-facing and the intracellular signaling domain may be cytoplasmic.

Figure 1B:
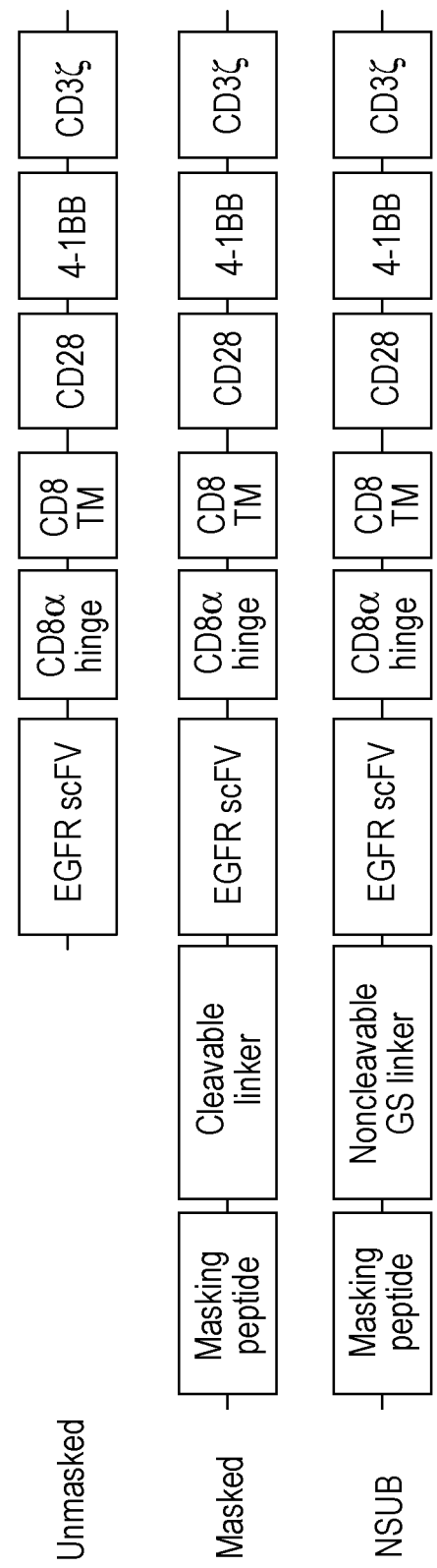

FIG. 1 shows a schematic of a masked chimeric antigen receptor of the invention.

Masking Peptides

The masking peptide comprises a mask and a cleavage site. In various embodiments, the masking peptides are specific for each antigen-specific targeting domain in the CAR. For example, each scFv specific to a target antigen will have a unique masking peptide sequence. The mask and the cleavage site are joined by a linker. The mask is specific/unique to the antigen-specific targeting domain of the CAR and blocks the binding of CAR to the antigen on the target cell until the mCAR is activated by cleaving the masking peptide at the cleavage site. An exemplary embodiment of the masked CAR is described in Table 1 and/or SEQ ID NO: 29.

Masking peptides may be 5 to 50 amino acids longs. In various embodiments, the masking peptides (comprising the mask, linker and cleavage site) are 2-5, 5-10, 5-15, 10-15, 10-25, 15-20, 15-25, 20-25, 20-30, 25-30, 25-35, 30-35, 35-40, 35-45, 40-45 or 45-50 amino acids long. In some embodiments, the masking peptides are 5, 10, 15, 20, 25, 30, 35, 40, 45 or 50 amino acids long. In an embodiment, mask in the masking peptide is specific for each antigen-specific targeting domain of the CAR. In some embodiments, the mask may be 2-5, 5-10, 5-15, 10-15, 10-25 amino acids long.

In an exemplary embodiment, the ASTD in the mCAR is specific for EGFR and the mask comprises or consists of or essentially consists of the sequence CISPRGCPDGPYVMY (SEQ ID NO: 1). In another exemplary embodiment, the ASTD in the mCAR is specific for EGFR and the mask comprises or consists of or essentially consists of the sequence QGQSGQCISPRGCPDGPYVMY (SEQ ID NO: 8). In another exemplary embodiment, the ASTD in the mCAR is specific for Her2 and the mask comprises or consists of or essentially consists of the sequence LLG-PYELWELSH (SEQ ID NO: 17). In further exemplary embodiments, the ASTD in the CAR is specific for GD2 ganglioside and the mask comprises or consists of or essentially consists of the sequence RCNPNMEPPRCWAAEGD (SEQ ID NO: 22) or (VCNPLTGALLCSAAEGD) (SEQ ID NO: 23). In additional exemplary embodiments, the ASTD in the CAR is specific for carbonic anhydrase 9 (CA-IX) and the mask comprises or consists of or essentially consists of the sequence LSTAFARV (SEQ ID NO: 24) or ALG-PGREYRAL (SEQ ID NO: 25).

Methods for screening for masks in masking peptides will be apparent to a person of skill in the art. In some embodiments, combinatorial approaches are used to design masked peptides. Combinatorial approaches comprise combining known masks (e.g. peptides that have been shown to bind to antibodies or other antigen-binding domains) with known antigen-binding domains (e.g. single-chain antibodies or other protein-binding domains). In some embodiments, de novo screening approaches are used to design masked peptides by screening peptides in, for example, bacterial-display peptide libraries, for their ability to mask antigen-specific binding domains in existing CARs. Suitable masking moieties are identified using any of a variety of known techniques. For example, peptide masking moieties are identified using the methods described in U.S. Patent Application Publication No. 2009/0062142 by Daugherty et al., the contents of which are hereby incorporated by reference in their entirety. With bacterial display screening, for example, masking peptide libraries are displayed on the cell surface by fusion to a bacterial membrane protein, such as OmpX. Transformed cells are incubated with a fluorophore-labeled antibody corresponding to the antigen-binding domain of the CAR, and bound cells are isolated by fluorescence-activated cell sorting. Bound cells are amplified, and the selection process is repeated for several rounds. Candidate masking peptide sequences are identified by sequencing of the selected clones. Other screening methods include phage display, as taught in Barbas, Carlos F., et al. *Phage display: a laboratory manual.* CSHL Press, 2004; mRNA display, as taught in Wilson, David S., Anthony D. Keefe, and Jack W. Szostak. "The use of mRNA display to select high-affinity protein-binding peptides." *Proceedings of the National Academy of Sciences* 98.7 (2001): 3750-3755; and yeast display, as taught in Boder, Eric T., and K. Dane Wittrup. "Yeast surface display for screening combinatorial polypeptide libraries." *Nature biotechnology* 15.6 (1997): 553-557.

In various embodiments, the cleavage site comprises a sequence that includes a substrate to a protease, for example a protease that is co-localized with the target antigen at the treatment site in a subject. In some embodiments, the cleavage site in the masking peptide is 2-5, 5-10, 5-15, 10-15, 5, 8, 10, 12 or 15 amino acids long. In an exemplary embodiment, the cleavage site comprises or consists of or essentially consists of the sequence LSGRSDNH (SEQ ID NO: 2) and is specific for uPA protease. In another exemplary embodiment, the cleavage site comprises or consists of or essentially consists of the sequence LSGRSDNHGSSGT (SEQ ID NO: 9) and is specific for uPA protease. Methods for selecting suitable cleavage sites suitable for use with the mCARs described herein will be apparent to a person of skill in the art. In some embodiments, the cleavage sites are substrates for proteases such as uPA, MT-SP1, Legumain. In some embodiments, the cleavage sites are substrates for proteases such as matrix metalloproteinases (MMPs). Examples of matrix metalloprotease (MMP) cleavable linker sequences include but are not limited to protease MMP-1 substrate VLVPMAMMAS (SEQ ID NO: 26), MMP-2 and/or MMP-9 substrate GPLGIAGQ (SEQ ID NO: 27) or PVGLIG (SEQ ID NO: 28).

Desirable characteristics of cleavage sites include but are not limited to non-toxicity to the subject, stability during systemic circulation in a subject, non-susceptibility to circulating proteases (such as thrombin, plasmin etc.) and are active at the intended site of treatment in the subject. Suitable substrates are identified using any of a variety of known techniques. For example, peptide substrates are identified using the methods described in U.S. Pat. No. 7,666,817 by Daugherty et al, the contents of which are hereby incorporated by reference in their entirety. (See also Boulware et al. "Evolutionary optimization of peptide substrates for proteases that exhibit rapid hydrolysis kinetics." Biotechnol Bioeng. 106.3 (2010): 339-46).

In an exemplary embodiment, the linker between the mask and the cleavage site comprises or consists of or essentially consists of the sequence GSSGGSGGSGGSG (SEQ ID NO: 10) and the linker that links the masking peptide to the CAR comprises or consists of or essentially consists of the sequence GSSGT (SEQ ID NO: 11).

In some embodiments, masked CAR (mCAR) reduces the ability of the CAR to bind to the target antigen at the treatment site in the subject such that the dissociation constant (Kd) of the CAR when linked to the masking peptide towards the target antigen is at least 20 times greater than the Kd of the CAR when not linked to the masking peptide towards the antigen. In some embodiments, masked CAR (mCAR) reduces the ability of the CAR to bind to the target antigen at the treatment site in the subject such that the dissociation constant (Kd) of the CAR when linked to the masking peptide towards the target antigen is at least 100 times greater than the Kd of the CAR when not linked to the masking peptide towards the antigen. In some embodiments, masked CAR (mCAR) reduces the ability of the CAR to bind to the target antigen at the treatment site in the subject such that the dissociation constant (Kd) of the CAR when linked to the masking peptide towards the target antigen is at least 1000 times greater than the Kd of the CAR when not linked to the masking peptide towards the antigen. In some embodiments, masked CAR (mCAR) reduces the ability of the CAR to bind to the target antigen at the treatment site in the subject such that the dissociation constant (Kd) of the CAR when linked to the masking peptide towards the target antigen is at least 1000 times greater than the Kd of the CAR when not linked to the masking peptide towards the antigen. In an exemplary embodiment, masked CAR (mCAR) reduces the ability of the EGFR-specific CAR to bind to EGFR at the treatment site in the subject such that the dissociation constant (Kd) of the EGFR-specific CAR when linked to the masking peptide towards EGFR is at least any of 20, 50, 100, 100 or 10,000 times greater than the Kd of the EGFR-specific CAR when not linked to the masking peptide towards the antigen.

In some embodiments, in the presence of the target antigen, the masking peptide reduces the ability of the CAR to bind target antigen by at least 95%, 90%, 85%, 80%, 75%, 70% or 65% when the cleavage site is uncleaved, as compared to when the cleavage site is cleaved when assayed in vitro using a target displacement assay such as, for example, the assay described in PCT Publication Nos. WO 2009/025846 and WO 2010/081173. In an exemplary embodiment, in the presence of EGFR, the masking peptide described in Table 1 and/or SEQ ID NO: 29 reduces the ability of the EGFT-specific CAR to bind EGFR by at least 95%, 90%, 85%, 80%, 75%, 70% or 65% when the cleavage site as shown in Table 1 (LSGRSDNH, SEQ ID NO:2) is uncleaved, as compared to when the cleavage site is cleaved.

Antigen-Specific Targeting Domains of Chimeric Antigen Receptors

The mCARs of the invention may target one or more antigens. The antigens targeted by the ASTD of the mCAR may be antigens on single diseased cell (such as a cancerous B-cell) or antigens that are expressed on separate cells that each contribute to the disease. The antigens targeted by the mCAR are antigens which are either directly or indirectly involved in the disease. The antibody comprising the ASTD of the mCAR may be specific for any antigen of choice. The antibody specific to the antigen may be the Fab fragment of the antibody or the single chain variable fragment (scFv) of the antibody.

For example, FIG. 1 shows an embodiment of the invention depicting a mCAR specific to EGFR and comprising a masking peptide and a cleavable linker. Using methods well known to one skilled in the art, the masking peptides are cloned upstream (i.e., to N-terminus) of the ASTD (such as scFvs). Further, the scFvs specific to antigens, may be cloned upstream (i.e., to N-terminus) of the CD28TM-41BBCSD-CD3zetaISD domains so long as the target-antigens are expressed on cells that are targetable by the genetically modified cells described below. In another embodiment, scFvs specific to antigens, may be cloned upstream (i.e., to N-terminus) of the CD8αhinge-CD8TM-CD28CSD-41BBCSD-CD3zetaISD (FIG. 1) domains so long as the target-antigens are expressed on cells that are targetable by the genetically modified cells described below. Such techniques are explained fully in the literature. (Sambrook et al, "Molecular Cloning: A Laboratory Manual" (1989), Current Protocols in Molecular Biology. Volumes I-III [Ausubel, R. M., ed. (1994)], Cell Biology: A Laboratory Handbook. Volumes I-III [J. E. Celis, ed. (1994))], Current Protocols in Immunology. Volumes I-III [Coligan, J. E., ed. (1994)], Oligonucleotide Synthesis. (M. J. Gait ed. 1984), Nucleic Acid Hybridization [B. D. Hames & S. J. Higgins eds. (1985)], Transcription And Translation [B. D. Hames & S. J. Higgins, eds. (1984)], Animal Cell Culture [R. I. Freshney, ed. (1986)], Immobilized Cells And Enzymes [IRL Press, (1986)], Practical Guide To Molecular Cloning B. Perbal (1984), Current Protocols in Immunology (J. E. Coligan, A. M. Kruisbeek, D. H. Margulies, E. M. Shevach and W. Strober, eds., 1991), Annual Review of Immunology as well as monographs in journals such as Advances in Immunology).

In one embodiment, the antigen-specific targeting domain comprises the full-length IgG heavy chain (specific for the target antigen) having the $V_H$, CH1, hinge, and the CH2 and CH3 (Fc) Ig domains, if the $V_H$ domain alone is sufficient to confer antigen-specificity ("single-domain antibodies"). The full length IgG heavy chain may be linked to the co-stimulatory domain and the intracellular signaling domain via the appropriate transmesmbrane domain. In an embodiment, an extracelluar spacer domain may be linked between the antigen-specific binding domain and the transmembrane domain.

In another embodiment, each antigen-specific targeting domain of the mCAR comprises one or more single chain antibody variable fragments (scFv). If more than one scFV is present in the mCAR, each scFV is specific for a different target antigen. scFvs, in which the C-terminus of one variable domain ($V_H$ or $V_L$) is tethered to the N-terminus of the other ($V_L$ or $V_H$, respectively) via a polypeptide linker, have been developed without significantly disrupting antigen binding or specificity of the binding. (Chaudhary et al., A recombinant single-chain immunotoxin composed of anti-Tac variable regions and a truncated diphtheria toxin. 1990 *Proc. Natl. Acad. Sci.*, 87:9491; Bedzyk et al. Immunological and structural characterization of a high affinity anti-fluorescein single-chain antibody. 1990 *J. Biol. Chem.*, 265: 18615). The linker connects the N-terminus of the $V_H$ with the C-terminus of $V_L$ or the C-terminus of $V_H$ with the N-terminus of $V_L$. These scFvs lack the constant regions (Fc) present in the heavy and light chains of the native antibody. In some embodiments, the scFvs are specific for at least two different antigens and are arranged in tandem and linked to the co-stimulatory domain and the intracellular signaling domain via a transmembrane domain. In an optional embodiment, an extracelluar spacer domain may be linked between the antigen-specific binding region and the transmembrane domain.

In another aspect, each scFv fragment may be fused to all or a portion of the constant domains of the heavy chain. The resulting antigen-specific targeting domain is joined to the co-stimulatory domain and the intracellular signaling domain via a transmembrane domain. In an optional embodiment, an extracelluar spacer domain may be linked between the antigen-specific binding domain and the transmembrane domain.

In a further embodiment, the one or more antigen-specific targeting domain of the mCAR comprises a divalent (or bivalent) single-chain variable fragment (di-scFvs, bi-scFvs). In mCARs comprising di-scFVs, two scFvs specific for the antigen are linked together by producing a single peptide chain with two $V_H$ and two $V_L$ regions, yielding tandem scFvs. (Xiong, Cheng-Yi; Natarajan, A; Shi, X B; Denardo, G L; Denardo, S J (2006). "Development of tumor targeting anti-MUC-1 multimer: effects of di-scFv unpaired cysteine location on PEGylation and tumor binding". *Protein Engineering Design and Selection* 19 (8): 359-367)). mCARs comprising one or more antigen-specific targeting domains would express two scFvs specific for each of the two antigens. The resulting antigen-specific targeting domain is joined to the co-stimulatory domain and the intracellular signaling domain via a transmembrane domain. In an optional embodiment, an extracelluar spacer domain may be linked between the antigen-specific binding domain and the transmembrane domain.

In an additional embodiment, each antigen-specific targeting domain of the mCAR comprises a diabody. In a diabody, the scFvs are created with linker peptides that are too short for the two variable regions to fold together, driving the scFvs to dimerize. Still shorter linkers (one or two amino acids) lead to the formation of trimers, the so-called triabodies or tribodies. Tetrabodies may also be used.

To create the mCARs of the present invention, antigen-specific targeting domains are connected to each other, either covalently or noncovalently, on a single protein molecule. An oligo- or polypeptide linker, an Fc hinge or membrane hinge region may be used to connect these domains to each other.

Co-Stimulatory Domains of Masked Chimeric Antigen Receptors

The mCARs of the invention may also comprise a co-stimulatory domain. This domain may enhance cell proliferation, cell survival and development of memory cells. The mCARs of the invention may comprise one or more co-stimulatory domains. Each co-stimulatory domain comprises the co-stimulatory domain of any one or more of, for example, members of the TNFR super family, CD28, CD137 (4-1BB), CD134 (OX40), Dap10, CD27, CD2, CD5, ICAM-1, LFA-1, Lck, TNFR-1, TNFR-II, Fas, CD30, CD40 or combinations thereof. Co-stimulatory domains from other proteins may also be used with the CARs of the invention. Additional co-stimulatory domains will be apparent to those of skill in the art and may be used in connection with alternate embodiments of the invention. If a mCAR comprises more than one co-stimulatory domain, these domains may be arranged in tandem, optionally separated by a linker.

Extracellular Spacer Domain of Masked Chimeric Antigen Receptor

The mCARs of the invention may further comprise an extracellular spacer domain. In some embodiments, this domain facilitates proper protein folding. The extracellular spacer domain comprises a hydrophilic region which is attached to the antigen-specific targeting domain and the transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions antibodies, artificial spacer sequences or combinations thereof. Examples of extracellular spacer domains include but are not limited to CD8α hinge, artificial spacers made of polypeptides such as Gly3, or CH1, CH3 domains of IgG's (such as human IgG4). Specifically, the extracellular spacer domain may be (i) a hinge, CH2 and CH3 regions of IgG4, (ii) a hinge region of IgG4, (iii) a hinge and CH2 of IgG4, (iv) a hinge region of CD8α, (v) a hinge, CH2 and CH3 regions of IgG1, (vi) a hinge region of IgG1 or (vi) a hinge and CH2 of IgG1 or a combination thereof. Additional extracellular spacer domains will be apparent to those of skill in the art and may be used in connection with alternate embodiments of the invention.

Transmembrane Domain of Masked Chimeric Antigen Receptors

The mCARs of the invention may also comprise a transmembrane domain. The transmembrane domain may comprise the transmembrane sequence from any protein which has a transmembrane domain, including any of the type I, type II or type III transmembrane proteins. The transmembrane domain of the mCAR of the invention may also comprise an artificial hydrophobic sequence. The transmembrane domains of the mCARs of the invention may be selected so as not to dimerize. Additional transmembrane domains will be apparent to those of skill in the art and may be used in connection with alternate embodiments of the invention.

Intracellular Signaling Domain of Masked Chimeric Antigen Receptors

The mCARs of the invention may also comprise an intracellular signaling domain. This domain may be cytoplasmic and may transduce the effector function signal and direct the cell to perform its specialized function. Examples of intracellular signaling domains include, but are not limited to, chain of the T-cell receptor or any of its homologs (e.g., chain, εR1γ and β chains, MB1 (Igα) chain, B29 (Igβ) chain, etc.), CD3 polypeptides (Δ, δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. Specifically, the intracellular signaling domain may be human CD3 zeta chain, FcγRIII, FcεRI, cytoplasmic tails of Fc receptors, immunoreceptor tyrosine-based activation motif (ITAM) bearing cytoplasmic receptors or combinations thereof. Additional intracellular signaling domains will be apparent to those of skill in the art and may be used in connection with alternate embodiments of the invention.

Linkers in mCARs

In some embodiments, two or more components of the mCARs of the invention are separated by one or more linkers. In some embodiments, the components of the masking peptide (mask and cleavage site) are separated by a linker sequence. In some embodiments, the masking peptide is linked to the CAR by a linker sequence. Linkers are oligo- or polypeptides region from about 1 to 100 amino acids in length, that link together any of the domains/regions of the CAR of the invention. In some embodiments, the linkers may be for example, 5-12 amino acids in length, 5-15 amino acids in length or 5 to 20 amino acids in length. Linkers may be composed of flexible residues like glycine and serine so that the adjacent protein domains are free to move relative to one another. Longer linkers, for example those longer than 100 amino acids, may be used in connection with alternate embodiments of the invention, and may be selected to, for example, ensure that two adjacent domains do not sterically interfere with one another. Examples of linkers which may be used in the instant invention include but are not limited to 2A linkers (for example T2A), 2A-like linkers or functional equivalents thereof.

As described above, the mCARs of the invention may be synthesized as single polypeptide chains. In an embodiment, the single polypeptide chain encoding the uncleaved mCAR has the structural arrangement from N-terminus to C-terminus, of: mask-linker-cleavage site-linker-antigen specific targeting domain-transmembrane domain-costimulatory domain-intracellular signaling domain. Additional sequences may be present between each domain to, for example, provide further flexibility and stability to the mCAR.

In an embodiment, the single polypeptide chain encoding the uncleaved mCAR has the structural arrangement from N-terminus to C-terminus, of: mask-linker-cleavage site-linker-antigen specific targeting domain-extracellular spacer domain-transmembrane domain-costimulatory domain-intracellular signaling domain. Additional sequences may be present between each domain to, for example, provide further flexibility and stability to the mCAR.

Targets of Antigen-Specific Targeting Domains of Chimeric Antigen Receptors

In some embodiments, the antigen-specific targeting domain of the mCAR targets antigens specific for cancer, inflammatory disease, neuronal-disorders, diabetes, cardiovascular disease, infectious diseases or a combination thereof. Examples of antigens which may be targeted by the mCARs of the invention include but are not limited to antigens expressed on B-cells, antigens expressed on carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases. The mCARs of the invention may be capable of redirecting the effector function of the expressing-cells to either of both of the target antigens. This feature of the construct may overcome the issue of antigen loss escape variants when targeting, for example, genetically unstable B-cell lineage malignancies using single antigen-specificity.

Antigens specific for cancer which may be targeted by the mCARs described herein include but are not limited to any one or more of 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, vimentin or combination thereof. Other antigens specific for cancer will be apparent to those of skill in the art and may be used in connection with alternate embodiments of the invention.

Antigens specific for inflammatory diseases which may be targeted by the mCARs described herein include but are not limited to any one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, *Lama glama*, LFA-1 (CD11a), MEDI-528, myostatin, OX-40, rhuMAb β7, scleroscin, SOST, TGF beta 1, TNF-α or VEGF-A. Other antigens specific for inflammatory diseases will be apparent to those of skill in the art and may be used in connection with alternate embodiments of the invention.

Antigens specific for neuronal disorders which may be targeted by the mCARs described herein include but are not limited to any one or more of beta amyloid or MABT5102A. Other antigens specific for neuronal disorders will be apparent to those of skill in the art and may be used in connection with alternate embodiments of the invention.

Antigens specific for diabetes which may be targeted by the mCARs described herein include but are not limited to any one or more of L-1β or CD3. Other antigens specific for diabetes or other metabolic disorders will be apparent to those of skill in the art and may be used in connection with alternate embodiments of the invention.

Antigens specific for cardiovascular diseases which may be targeted by the mCARs described herein include but are not limited to any one or more of C5, cardiac myosin, CD41 (integrin alpha-IIb), fibrin II, beta chain, ITGB2 (CD18) and sphingosine-1-phosphate. Other antigens specific for cardiovascular diseases will be apparent to those of skill in the art and may be used in connection with alternate embodiments of the invention.

Antigens specific for infectious diseases which may be targeted by the mCARs described herein include but are not limited to any one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-α. Other antigens specific for infectious diseases will be apparent to those of skill in the art and may be used in connection with alternate embodiments of the invention.

Further examples of target antigens which may be targeted by the mCARs described include but are not limited to surface proteins found on cancer cells in a specific or amplified fashion (e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas), or viral proteins (e.g. gp120 and gp41 envelope proteins of HIV, envelope proteins from the Hepatitis B and C viruses, the glycoprotein B and other envelope glycoproteins of human cytomegalovirus, the envelope proteins from oncoviruses such as Kaposi's sarcoma-associated Herpes virus). Other potential targets of the CARs of the invention include CD4, where the ligand is the HIV gp120 envelope glycoprotein, and other viral receptors, for example ICAM, which is the receptor for the human rhinovirus, and the related receptor molecule for poliovirus.

Additional targets of the mCARs of the invention include antigens involved in B-cell associated diseases. Yet further targets of the mCARs of the invention will be apparent to those of skill in the art and may be used in connection with alternate embodiments of the invention.

Genetically Engineered Cells

The invention also provides genetically engineered cells which comprise and stably express the mCAR described herein. The mCAR expressed by the genetically engineered cell comprises a masking peptide, at least one antigen-specific targeting domain, an optional extracellular domain, a transmembrane domain, one or more co-stimulatory domains and an intracellular signaling domain. The polynucleotide sequence encoding the mCAR may also comprise an N-terminal signal sequence.

The genetically engineered cells express a mCAR described herein. In one embodiment, the antigen-specific targeting domains comprise target-specific antibodies or functional equivalents or fragments or derivatives thereof. The antigen-specific antibody may be the Fab fragment of the antibody or the single chain variable fragment (scFv) of the antibody.

Genetically engineered cells which may comprise and express the mCARs of the invention include, but are not limited to, T-lymphocytes (T-cells), naïve T cells ($T_N$), memory T cells (for example, central memory T cells ($T_{CM}$), effector memory cells ($T_{EM}$)), natural killer cells, hematopoietic stem cells and/or pluripotent embryonic/induced stem cells capable of giving rise to therapeutically relevant progeny. In an embodiment, the genetically engineered cells are autologous cells. By way of example, individual T-cells of the invention may be CD4+/CD8−, CD4−/CD8+, CD4−/CD8− or CD4+/CD8+. The T-cells may be a mixed population of CD4+/CD8− and CD4−/CD8+ cells or a population of a single clone. CD4+T− cells of the invention may produce IL-2, IFNγ, TNFα and other T-cell effector cytokines when co-cultured in vitro with cells expressing the target antigens. $CD8^+$ T-cells of the invention may lyse antigen-specific target cells when co-cultured in vitro with the target cells. In some embodiments, T cells may be any one or more of $CD45RA^+$ $CD62L^+$ naïve cells, $CD45RO^+$ $CD62L^+$ central memory cells, $CD62L^-$ effector memory cells or a combination thereof (Berger et al., Adoptive transfer of virus-specific and tumor-specific T cell immunity. *Curr Opin Immunol* 2009 21(2)224-232).

Genetically modified cells may be produced by stably transfecting cells with DNA encoding the mCAR described herein. Viral vectors are commonly used to carry heterologous genes into cells (e.g., T-cells). Examples of viral vectors which may be used to generate genetically modified cells include but are not limited to SIN lentiviral vectors, retroviral vectors, foamy virus vectors, adeno-associated virus (AAV) vectors and/or plasmid transposons (e.g., sleeping beauty transposon system).

Various methods produce stable transfectants which express the mCARs of the invention. In one embodiment, a method of stably transfecting and re-directing cells is by electroporation using naked DNA. By using naked DNA, the time required to produce redirected cells may be significantly reduced. Additional methods to genetically engineer cells using naked DNA encoding the mCAR of the invention include but are not limited to chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). The transfected cells demonstrating presence of a single integrated un-rearranged vector and expression of the mCAR may be expanded ex vivo. In one embodiment, the cells selected for ex vivo expansion are $CD8^+$ and demonstrates the capacity to specifically recognize and lyse antigen-specific target cells.

Viral transduction methods may also be used to generate redirected cells which express the mCAR of the invention. Cell types that may be used to generate genetically modified cells expressing the mCAR of the invention include but are not limited to T-lymphocytes (T-cells), natural killer cells, hematopoietic stem cells and/or pluripotent embryonic/induced stem cells capable of giving rise to therapeutically relevant progeny.

Stimulation of the T-cells by an antigen under proper conditions results in proliferation (expansion) of the cells and/or production of IL-2. The cells comprising the mCAR of the invention will expand in number in response to the binding of one or more antigens to the antigen-specific targeting domains of the mCAR. The invention also provides a method of making and expanding cells expressing a mCAR. The method comprises transfecting or transducing the cells with the vector expressing the mCAR and stimulating the cells with cells expressing the target antigens, recombinant target antigens, or an antibody to the receptor to cause the cells to proliferate, so as to make and expand T-cells. In an embodiment, the cells may be any one or more of T-lymphocytes (T-cells), natural killer (NK) cells, hematopoietic stem cells (HSCs) or pluripotent embryonic/induced stem cells capable of giving rise to therapeutically relevant progeny.

Therapeutic Methods

Provided herein are methods for treating a disease associated with the antigen targeted by the mCAR described herein in a subject in need thereof. The method comprises providing a composition comprising the mCAR described herein and administering an effective amount of the composition so as to treat the disease associated with the antigen in the subject.

Provided herein are methods for treating, inhibiting, slowing progression of and/or preventing metastasis of cancer in a subject in need thereof. The method comprises providing a composition comprising the mCAR described herein and administering an effective amount of the composition so as to treat, inhibit, slow progression of and/or prevent metastasis of cancer in the subject.

In some embodiments, the composition comprises a polynucleotide encoding the mCAR, a protein comprising the mCAR or genetically modified cells comprising the mCAR. In another embodiment, the genetically modified cells of the composition are T-lymphocytes (T-cells), naïve T cells ($T_N$), memory T cells (for example, central memory T cells ($T_{CM}$), effector memory cells ($T_{EM}$)), natural killer (NK) cells, hematopoietic stem cells (HSCs) or pluripotent embryonic/induced stem cells capable of giving rise to therapeutically relevant progeny, which express the mCAR of the invention. The compositions of the invention may be administered alone or in conjunction with existing therapies. If other therapies are used in conjunction, the compositions of the invention may be administered concurrently or sequentially with the other existing therapies.

In some embodiments, treating, inhibiting, slowing progression of and/or preventing metastasis of cancer in a subject in need thereof includes administering an effective amount of the composition comprising mCAR described herein in conjunction with existing therapies. In various embodiments, the composition comprising mCAR may be administered sequentially or simultaneously with existing therapies. Examples of existing cancer treatment include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or combinations thereof.

Examples of chemotherapeutic agents include but are not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof.

In various embodiments, the effective amount of the composition comprising the mCARs described herein is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Typical dosages of an effective amount of the mCARs described herein can be in the ranges recommended by the manufacturer where known therapeutic compounds are used, and also as indicated to the skilled artisan by the in vitro responses or responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, such as biopsied malignant tumors, or the responses observed in the appropriate animal models. In various embodiments, the compositions of the invention comprising the mCARs described herein may be administered once a day (SID/QD), twice a day (BID), three times a day (TID), four times a day (QID), or more, so as to administer an effective amount of the mCAR to the subject, where the effective amount is any one or more of the doses described herein.

Pharmaceutical Compositions

In various embodiments, the present invention provides pharmaceutical compositions comprising a pharmaceutically acceptable excipient and a therapeutically effective amount of the mCAR described herein. The mCAR in the composition may be any one or more of a polynucleotide encoding the mCAR, a protein comprising the mCAR or genetically modified cells comprising the mCAR. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, intravenous, intramuscular, intraperitoneal, inhalation, transmucosal, transdermal, parenteral, implantable pump, continuous infusion, topical application, capsules and/or injections.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Experimental Methods

Cell line construction: K562-EGFR cell line was generated by stable transduction of K562 cells with VSVg pseudotyped lentivectors. The cDNA of human EGFR (GE Healthcare) was amplified and cloned into the lentiviral plasmid FUW to generate FUW-EGFR. The lentivectors were then produced and used to transduce K562 cells. The transduced cells were stained with PE/Cy7 anti-human EGFR Antibody (Biolegend) and sorted to yield a population of EGFR expressing K562 cells. K562-CD19 cell line was generated using the similar method.

Plasmid construction: The lentiviral vector pCCW-EGFR CAR was constructed by Gibson assembling EGFR scFv sequence, CD28 transmembrane domain—41BB—CD3z costimulatory domains and backbone pCCW vector. Plasmid pCCW-mask EGFR CAR was constructed based on pCCW-EGFR CAR, with addition of DNA sequence optimized to express masking peptide and protease substrate sequence flanked by GS linker (SEQ ID NO: 12))
(QGQSGQ-CISPRGCPDGPYVMY-GSSGGSGGSGGSG-<u>LSGRSDNH</u>-GSSGT in the N terminus of EGFR scFv region. Mask peptide is underlined; substrate region is dotted underlined.

Lentivector Production:

Lentivectors were prepared by transient transfection of 293T cells using a standard calcium phosphate precipitation protocol. 293T cells cultured in 6-cm tissue culture dishes were transfected with 5 μg of the lentiviral backbone plasmid pCCW-EGFR CAR or pCCW-mask EGFR CAR, along with 2.5 μg of the envelope plasmid VSVG and the packaging plasmids pMDLg/pRRE and pRSV-Rev. The viral supernatants were harvested 48 h post-transfection and filtered through a 0.45-μm filter (Corning).

Lentivector Transduction of Cell Lines:

Jurkat or Jurkat-NFAT-GFP reporter cells (1E5 per well) were seeded in a 24-well culture dish and spin-infected with freshly harvested viral supernatants (2 ml per well) at 2,500 rpm and 25° C. for 90 min. Then the supernatants were replaced with fresh culture medium and incubated for 3 days at 37° C. with 5% of CO2. The expression of CAR was measured by flow cytometry.

Flow Cytometry:

For detection of CAR expression, the CAR-Jurkat cells were washed twice in PBS containing 4% bovine serum albumin (wash buffer), stained with 2 μg/ml recombinant human EGFR-Fc (R&D Systems) at 4° C. for 30 min, washed twice and then stained with R-Phycoerythrin AffiniPure F(ab')$_2$ Fragment Goat Anti-Human IgG, Fcγ Fragment Specific (Jackson ImmunoResearch) at 4° C. for 30 min. Cells were washed twice and resuspended in PBS. Fluorescence was assessed using a Miltenyi Biotec flow cytometer and data were analyzed with FlowJo software.

Proteolytic Activation of Mask EGFR CAR:

Protease-mediated activation of mask EGFR CAR was achieved by incubating 1e5 mask EGFR CAR-Jurkat reporter cells with different concentrations of protease uPA (urokinase-type plasminogen activator, R&D Systems) in PBS for 1 hour at room temperature. The cells were washed with PBS twice and used in further experiments.

Co-Culture of CAR-Jurkat Reporter Cells with Target Cells:

1e5 EGFR CAR/mask EGFR CAR-Jurkat reporter cells were seeded together with 2e5 target cells K562-EGFR or MDA-MB-231 in the round-bottom 96-well plate in 200 µl C10 medium. CD19 CAR-Jurkat reporter cells were cocultured together with K562-CD19 cells. The cell mixture was incubated at 37° C. for 5 hours. Cells were washed and resuspended in PBS. The GFP fluorescence was analyzed by flow cytometer.

An anti-EGFR mCAR having the sequence shown in Table 1 below was made by the inventors.

TABLE 1

Mask is in bold and cleavage site is underlined ("Desnoyers, L.R. et al. Tumor-specific activation of an EGFR-targeting probody enhances therapeutic index. Sci Transl Med 5, 207ra144 (2013)).

| | |
|---|---|
| Mask + cleavable linker | QGQSGQ CISPRGCPDGPYVMY GSSGGSGGSGGSG <u>LSGRSDNH</u> GSSGT (SEQ ID NO: 12) |
| VL cetuximab | QILLTQSPVILSVSPGERVSFS CRASQSIGTNIHWYQQRTNGSP RLLIKYASESISGIPSRFSGSG SGTDFTLSINSVESEDIADYYC QQNNNWPTTFGAGTKLELKR (SEQ ID NO: 3) |
| GS linker | GGGGSGGGGSGGGGS (SEQ ID NO: 10) |
| VH cetuximab | QVQLKQSGPGLVQPSQSLSITC TVSGFSLTNYGVHWVRQSPGKG LEWLGVIWSGGNTDYNTPFTSR LSINKDNSKSQVFFKMNSLQSN DTAIYYCARALTYYDYEFAYWG QGTLVTVSS (SEQ ID NO: 4) |
| CD8 hinge | TTTPAPRPPTPAPTIASQPLSL RPEACRPAAGGAVHTRGLDFAC DI (SEQ ID NO: 13) |
| CD28 TM + signaling | FWVLVVVGGVLACYSLLVYVAF IIFWVRSKRSRGGHSDYMNMTP RRPGPTRKHYQPYAPPRDFAAY RS (SEQ ID NO: 14) |
| 4-1BB signaling | RFSVVKRGRKKLLYIFKQPFMR PVQTTQEEDGCSCRFPEEEEGG CEL (SEQ ID NO: 15) |
| CD3z signaling | RVKFSRSADAPAYQQGQNQLYN ELNLGRREEYDVLDKRRGRDPE MGGKPRRKNPQEGLYNELQKDK MAEAYSEIGMKGERRRGKGHDG LYQGLSTATKDTYDALHMQALP PR (SEQ ID NO: 16) |

Figure 2:
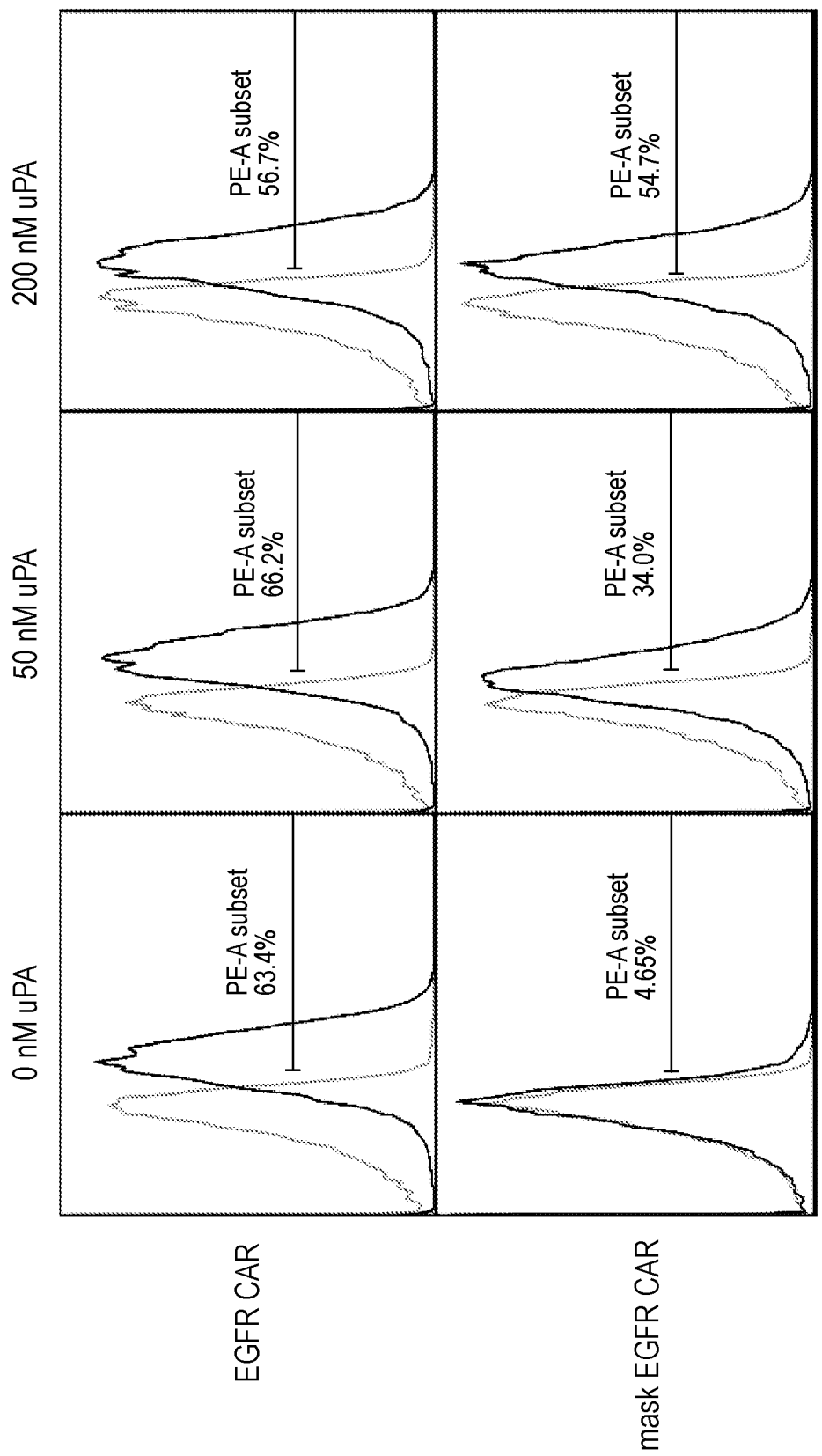
FIG. 2 depicts, in accordance with an embodiment of the invention, the binding capacity to EGFR protein of anti-EGFR CAR transduced Jurkat cells. Jurkat cells were transduced with lentivectors encoding EGFR CAR or mask EGFR CAR, respectively. The CAR-Jurkat cells were stained with recombinant human EGFR-Fc and then goat-anti-human Fc antibody as secondary antibody (black) or $2^{nd}$ antibody only as background (grey).

Jurkat cells were transduced with anti-EGFR mCAR and the binding capacity of anti-EGFR mCAR to EGFR protein was analyzed. As shown in FIG. 2, the binding capacity to rhEGFR was largely diminished in mask EGFR CAR compared to parental anti-EGFR CAR, but could be restored after the cleavage of protease uPA.

Figure 3:
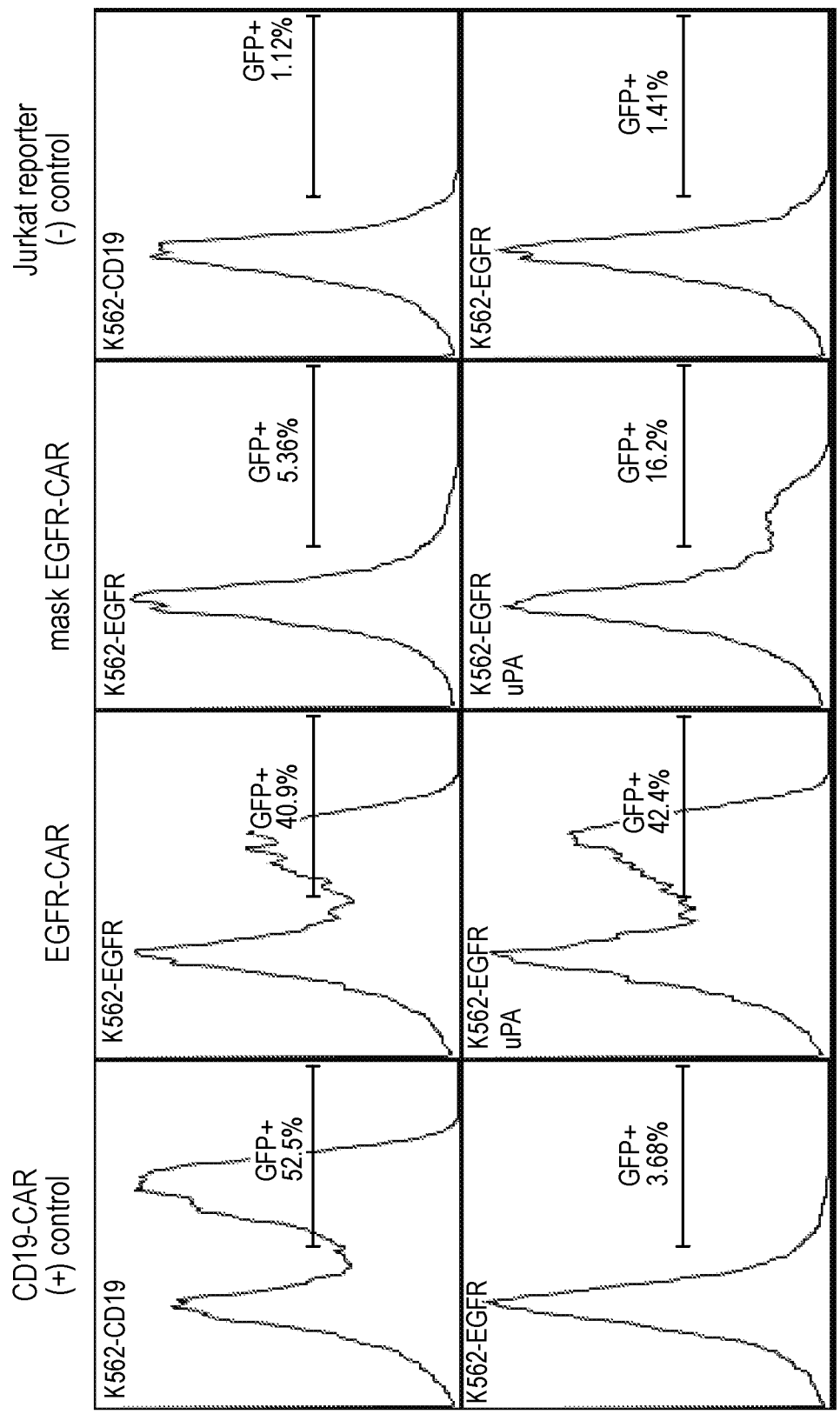
FIG. 3 depicts, in accordance with an embodiment of the invention, activation of CAR-Jurkat-NFAT-GFP reporter cells by coculture with the corresponding target cells K562-EGFR or K562-CD19 cells. Jurkat reporter cells were transduced with lentivectors encoding EGFR CAR, mask EGFR CAR or CD19 CAR respectively. The CAR-Jurkat reporter cells were cocultured with their target cells. The activation of CAR-Jurkat reporter cells was evaluated according to the GFP expression. The activation of mask EGFR CAR was diminished but can be partially regained after the cleavage of protease uPA (50 nM).

Jurkat-NFAT-GFP reporter cells were transduced with anti-EGFR mCAR and the activation of anti-EGFR mCAR (hereby the GFP expression in the reporter cells) was analyzed. As shown in FIG. 3, the activation of mask EGFR CAR was diminished compared to parental anti-EGFR CAR and partially regained after the cleavage of the protease uPA.

Figure 4:
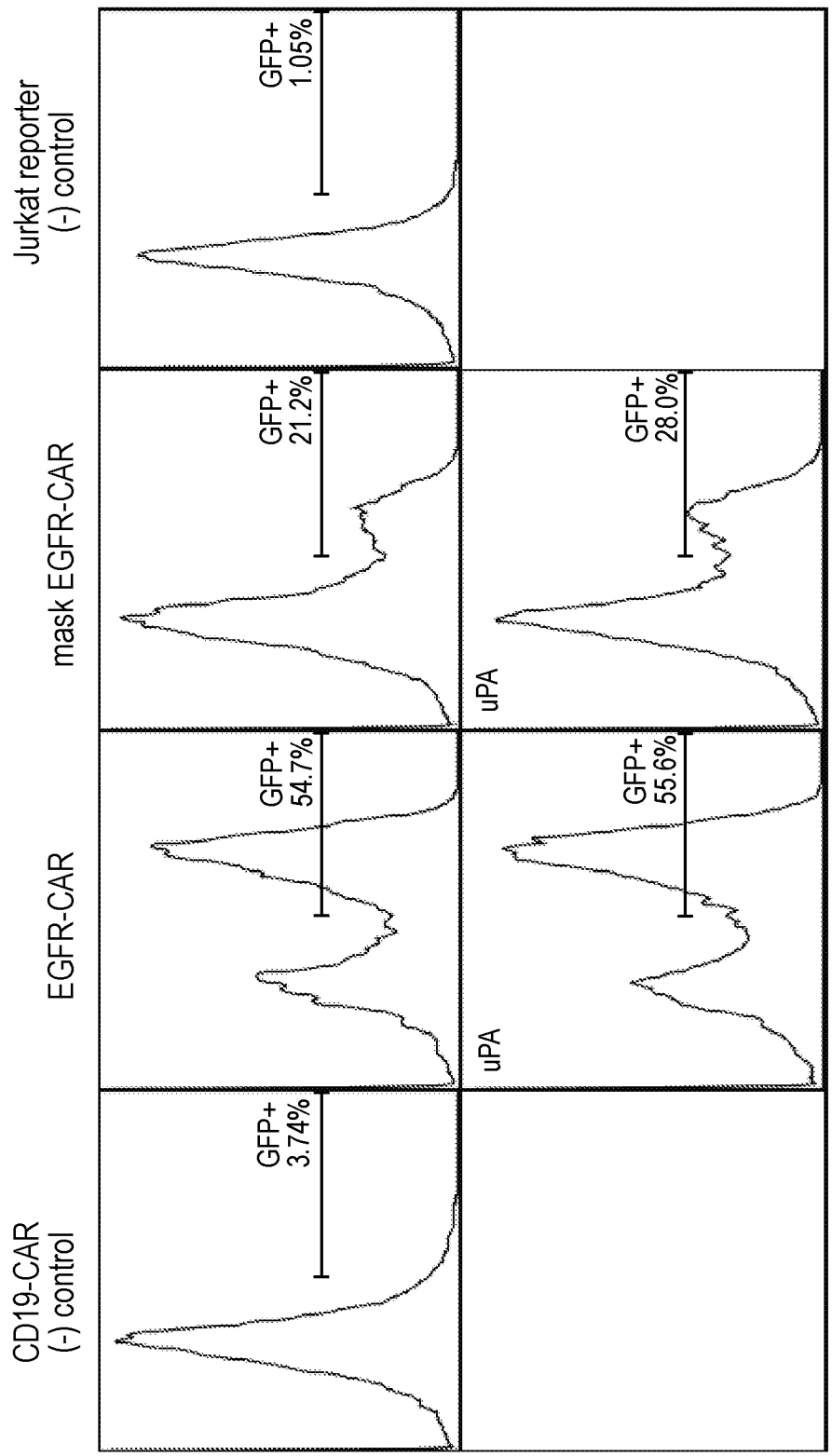
FIG. 4 depicts, in accordance with an embodiment of the invention, activation of CAR-Jurkat-NFAT-GFP reporter cells by coculture with the breast cancer cells MDA-MB-231. The endogenous secretion of proteases from MDA-MB-231 cells can partially activate mask EGFR CAR, while the treatment of uPA (50 nM) can enhance the activation signal.

As shown in FIG. 4, in the presence of breast cancer cells MDA-MB-231, which secretes endogenous proteases, mask EGFR CAR was partially activated, and treatment with uPA can further enhance the activation.

Figure 5:
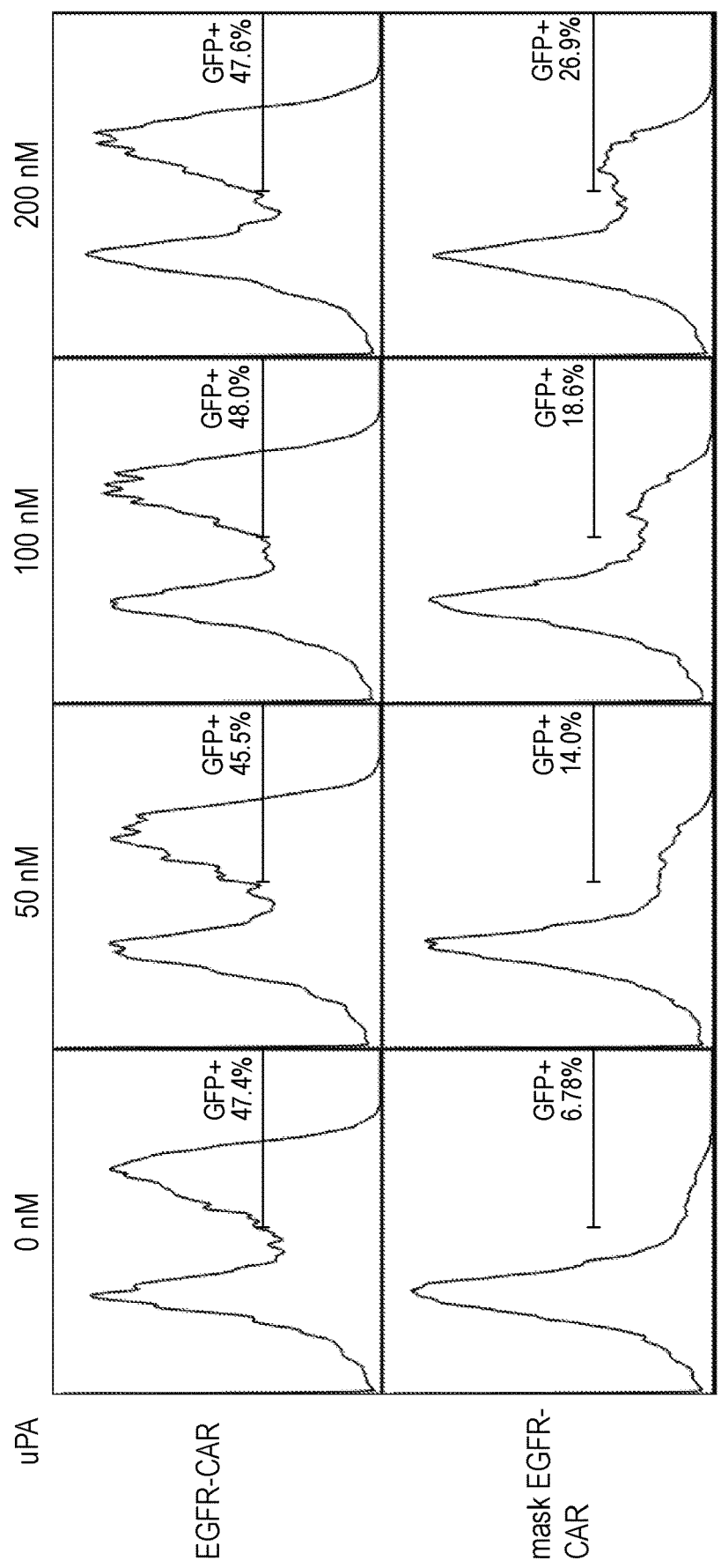
FIG. 5 depicts, in accordance with an embodiment of the invention, titration of uPA concentration to recover the activation of mask EGFR CAR-Jurkat reporter cells. Treatment with higher concentrations of uPA renders more activated mask EGFR CAR-Jurkat reporter population, evaluated by its GFP expression after stimulation with target K562-EGFR cells.

As shown in FIG. 5, treatment with higher concentrations of uPA leads to more activation of mask EGFR CAR.

Example 2

Masked HER-Specific CARs Using Combinatorial Design and De Novo Screening

Combinatorial design: Masked Her2-targeted CARs were generated by linking the trastuzumab-binding peptide, LLG-PYELWELSH (SEQ ID NO: 17), (Jiang, B. et al. A novel peptide isolated from a phage display peptide library with trastuzumab can mimic antigen epitope of HER-2. *J Biol Chem* 280, 4656-4662 (2005)) to the tumor-specific cleavage sequence, LSGRSDNH (SEQ ID NO: 2) (Desnoyers, L. R. et al. Tumor-specific activation of an EGFR-targeting probody enhances therapeutic index. *Sci Transl Med* 5, 207ra144 (2013). This cleavable mask was fused to the N-terminus of a single-chain antibody CAR derived from the trastuzumab antibody (Zhao, Y. et al. A Herceptin-Based Chimeric Antigen Receptor with Modified Signaling Domains Leads to Enhanced Survival of Transduced T Lymphocytes and Antitumor Activity. *The Journal of Immunology* 183, 5563-5574 (2009)). These CARs were tested for on-target and off-target activity using a T cell reporter line cocultured with Her2+ target cells.

De novo screening: Masking peptides were selected from a bacterial-display peptide library_ENREF_4 (Rice, J. J., Schohn, A., Bessette, P. H., Boulware, K. T. & Daugherty, P. S. Bacterial display using circularly permuted outer membrane protein OmpX yields high affinity peptide ligands. *Protein Science* 15, 825-836 (2006)) based on their ability to bind to a trastuzumab-based Her2-specific CAR (Zhao, Y. et al. A Herceptin-Based Chimeric Antigen Receptor with Modified Signaling Domains Leads to Enhanced Survival of Transduced T Lymphocytes and Antitumor Activity. *The Journal of Immunology* 183, 5563-5574 (2009)). Positive selection against Jurkat T cell lines stably expressing the Her2-specific CAR was followed by negative selection against the base Jurkat cell line. Isolated clones were sequenced and unique peptides were cloned into the N-terminus of the Her2 CAR by a cleavable linker. Masking CARs were selected by activity against Her2+ target cells in the presence of tumor-specific proteases and lack of activity in the absence of proteases.

Example 3

Masked Chimeric Antigen Receptor (mCAR) for Tumor-Specific Activation

Epidermal growth factor receptor (EGFR) is an attractive target for cancer therapy because of its wide overexpression in many epithelial tumors and the inverse correlation between EGFR expression and clinical outcome. Considerable success has been achieved through the development of small molecule inhibitors and monoclonal antibodies targeting EGFR, although treatment toxicities are observed in skin, kidney, and gastrointestinal system, as a result of EGFR expression in these healthy tissues. For example, cetuximab, a human mouse chimeric monoclonal antibody against human EGFR, has been approved for use in colon and head and neck cancers, but skin rash and diarrhea are the most common side effects resulting from endogenous EGFR expression in epithelial tissues. One method of improving the therapeutic index of cetuximab is the development of a probody, an antibody-based prodrug that remains unresponsive in healthy environment, but become activated in tumors by tumor-associated protease.

Herein, we constructed an EGFR-specific CAR using the sequence from the cetuximab-derived probody. This masked CAR (mCAR) contains an N-terminal masking peptide capable of blocking the antibody binding site to EGFR and a linker sensitive to tumor-associated proteases. This design enables CAR-T cells to remain inert upon encountering antigen in healthy tissues, but become activated in the tumor microenvironment by exposing antigen binding site through proteolytic cleavage, thereby allowing the recognition and killing of tumor cells.

Experimental Methods

Construction of Plasmids.

The retroviral vector encoding unmasked EGFR CAR (RV-umCAR) was constructed based on the MP71 retroviral vector (Engels, B. et al. (2003). Retroviral vectors for high-level transgene expression in T lymphocytes. *Hum Gene Ther* 14: 1155-1168). The RV-umCAR vector consisted of the following components in frame from 5' end to 3' end: the MP71 retroviral backbone, a NotI site, the anti-EGFR scFv light chain variable region, a GS linker, the anti-EGFR scFv heavy chain variable region, the hinge and transmembrane regions of the CD8α molecule, the cytoplasmic domains of CD28 and 4-1BB (CD137), CD3ζ signaling domain and an EcoRI site.

The anti-EGFR scFv portion in the unmasked CAR was derived from the amino acid sequence of cetuximab. The corresponding DNA sequence of the scFv was codon-optimized for its optimal expression in human cells using the online codon optimization tool and was synthesized by Integrated DNA Technologies (Coralville, Iowa). The unmasked EGFR CAR sequence was generated by Gibson assembly of all the fragments using the Gibson Assembly Cloning Kit from New England Biolab (Ipswich, Mass.) and then ligated into the MP71 backbone vector via NotI and EcoRI. The primers used in the Gibson assembly are as follows: forward primer (NotI), tta cGC GGC CGC gcc acc atg get ctg cct gt (SEQ ID NO: 30); reverse primer (EcoRI), tta GAA TTC tca tct tgg tgg cag agc ctg c (SEQ ID NO: 31). The upper case represents the target sequence for restriction enzyme digestion.

The masked and NSUB EGFR CAR constructs were cloned based on the unmasked EGFR CAR construct. The DNA sequence that encodes the masking peptide (underlined) and protease substrate sequence (dotted underlined) flanked by GS linker (amino acid sequence:

(SEQ ID NO: 12))
QGQSGQCISPRGCPDGPYVMY-GSSGGSGGSGGSG-LSGRSDNHGSSGT, as derived from a previous report, (Desnoyers, L R, et al. (2013). Tumor-specific activation of an EGFR-targeting probody enhances therapeutic index. *Sci Transl Med* 5:207ra144) were codon-optimized and then cloned into the N-terminus of scFv region in the unmasked CAR construct.

For the NSUB CAR construct, the protease substrate sequence was replaced by a GS linker sequence (dotted underlined)

(SEQ ID NO: 32))
QGQSGQCISPRGCPDGPYVMY-GSSGGSGGSGGSG-GGSGGGSGGSSGT and then cloned into N-terminal of unmasked CAR construct.

The envelope plasmid (pGALV) encoding gibbon ape leukemia virus glycoprotein (GALV) was constructed by the following steps. The cDNA of GALV was PCR-amplified from the genomic DNA of PG13 cell lines (Ghani, K, et al. (2009). Efficient human hematopoietic cell transduction using RD114- and GALV-pseudotyped retroviral vectors produced in suspension and serum-free media. *Hum Gene Ther* 20:966-974). The primers used for the cloning are forward primer (EcoRI), tat GAA TTC gcc acc atg gta ttg ctg cct ggg tcc (SEQ ID NO: 18) and reverse primer (EcoRI), gcg GAA TTC tta aag gtt acc ttc gtt ctc tag ggc (SEQ ID NO: 19). The resulting PCR fragment was then cloned into the pHCMV plasmid backbone from Addgene (Cambridge, Mass.) via the EcoRI site.

The lentiviral vector encoding human EGFR (FUW-EGFR) was generated by insertion of the cDNA of PCR-amplified human EGFR into the pENTR plasmid via SalI and XbaI, and then the EGFR gene was cloned into lentiviral vector FUW via LR reaction using the Gateway cloning kit from Thermo Fisher Scientific (Grand Island, N.Y.). The primers used for the cloning are forward primer (SalI), tat GTC GAC atg cga ccc tcc ggg acg gcg GAA TTC tta aag gtt acc ttc gtt ctc tag ggc (SEQ ID NO: 20), and reverse primer (XbaI), tcg TCT AGA cct tca ctg tgt ctg caa atc tgc c (SEQ ID NO: 21).

Cell Lines and Culture Media.

Cell lines K562, 293T and MDA-MB-231 were obtained from ATCC. Lung cancer line NCI-H292 was kindly provided by Dr. Ite Laird-Offringa (University of Southern California, Los Angeles, Calif.). The K562-EGFR cell line was generated by transduction of the parental K562 cells with lentiviral vector FUW-EGFR. The transduced K562 cells were stained with anti-human EGFR antibody (BioLegend, San Diego, Calif.) and sorted to yield a population of EGFR overexpressing K562 cells.

K562 and K562-EGFR cells were maintained in R10 medium consisting of RPMI-1640 medium supplemented with 10% fetal bovine serum (FBS), 2 mM L-glutamine, 10 mM HEPES, 100 U/ml penicillin and 100m/ml streptomycin. The 293T and MDA-MB-231 cells were cultured in D10 medium consisting of DMEM medium supplemented with 10% FBS, 2 mM L-glutamine, 100U/ml penicillin and 100m/ml streptomycin. All of the above cell culture media and additives were purchased from Hyclone (Logan, Utah). Human peripheral blood mononuclear cells (PBMCs) were cultured in T cell medium (TCM), which is composed of X-Vivo 15 medium (Lonza, Walkersville, Md.) supplemented with 5% human AB serum (GemCell, West Sacramento, Calif.), 1% HEPES (Gibco, Grand Island, N.Y.), 1% Pen-Strep (Gibco), 1% GlutaMax (Gibco), and 0.2% N-Acetyl Cysteine (Sigma-Aldrich, St. Louis, Mo.).

Retroviral Vector Production.

Retroviral vectors were prepared by transient transfection of 293T cells using a standard calcium phosphate precipitation protocol. 293T cells cultured in 15-cm tissue culture dishes were transfected with 37.5m of the retroviral backbone plasmid, along with 18.75 µg of the envelope plasmid pGALV and 30 µg of the packaging plasmid encoding gag-pol. The viral supernatants were harvested 48h and 72h post-transfection and filtered through a 0.45-µm filter (Corning, Corning, N.Y.) before use.

T Cell Transduction and Expansion.

Frozen human peripheral blood mononuclear cells (PBMCs) were obtained from AllCells (Alameda, Calif.). PBMCs were thawed in TCM and rested overnight. Before retrovial transduction, PBMCs were activated for 2 days by culturing with 50 ng/ml OKT3, 50 ng/ml anti-CD28 antibody and 10 ng/mL recombinant human IL-7 and IL-15 (PeproTech, Rocky Hill, N.J.). For transduction, freshly harvested retroviral supernatant was spin-loaded onto nontissue culture-treated 12-well plates coated with 15 µg retronectin per/well (Clontech Laboratories, Mountain View, Calif.) by centrifuging 2 hours at 2000×g at 32° C. The spin-loading of vectors was repeated once with fresh viral supernatant (Kochenderfer, J N, et al. (2009). Construction and preclinical evaluation of an anti-CD19 chimeric antigen receptor. *J Immunother* 32:689-702). Activated PBMCs were resuspended at the concentration of $5 \times 10^5$/ml with fresh TCM complemented with 10 ng/mL recombinant human IL-7 and IL-15 and added to the vector-loaded plates. The plates were spun at 1000×g at 32° C. for 10 minutes and incubated overnight at 37° C., and 5% $CO_2$. The same transduction procedure was repeated on the following day. During ex vivo expansion, culture medium was replenished and cell density was adjusted to $5 \times 10^5$/ml every two days. In this study, it should be noted that the combination of cytokines IL-7 and IL-15 were used for ex vivo expansion of CAR-T cells instead of IL-2, which is more widely used in experimental and clinical protocols. We chose this cytokine condition because it was reported that genetically engineered T cells cultured in the presence of IL-7 and IL-15 resulted in improved engraftment in NSG mice (Cieri, N, et al. (2013). IL-7 and IL-15 instruct the generation of human memory stem T cells from naive precursors. *Blood* 121:573-584; Alcantar-Orozco, et al. (2013). Potential limitations of the NSG humanized mouse as a model system to optimize engineered human T cell therapy for cancer. *Hum Gene Ther Methods* 24:310-320).

Surface Immunostaining and Flow Cytometry.

To detect EGFR CAR expression on the cell surface, cells were stained with either protein L or recombinant human EGFR-Fc fusion protein (rhEGFR-Fc). Before FACS staining, $1 \times 10^6$ cells were harvested and washed three times with FACS buffer (PBS containing 4% bovine serum albumin fraction V). For protein L staining, cells were stained with 0.5 µg of biotinylated protein L (GeneScript, Piscataway, N.J.) at 4° C. for 30 minutes (Zheng, Z L, et al (2012). Protein L: a novel reagent for the detection of Chimeric Antigen Receptor (CAR) expression by flow cytometry. *Journal of Translational Medicine* 10:29). Cells were washed with FACS buffer three times and then incubated with 0.1 µg of APC-conjugated streptavidin (BioLegend, San Diego, Calif.) in FACS buffer at 4° C. for 10 minutes and washed three times. For rhEGFR-Fc staining, cells were stained with 2 µg/ml recombinant human EGFR-Fc (R&D Systems, Minneapolis, Minn.) in FACS buffer at 4° C. for 30 min, washed twice and then stained with PE-AffiniPure F(ab')$_2$ fragment of goat anti-human IgG (Jackson ImmunoResearch, West Grove, Pa.) in FACS buffer at 4° C. for 30 min. Cells were washed twice and resuspended in PBS. Fluorescence was assessed using a Miltenyi Biotec flow cytometer and all the FACS data were analyzed with FlowJo software.

Proteolytic Activation of Masked EGFR CAR.

Protease-mediated activation of masked EGFR CAR was achieved by incubating $1 \times 10^6$ masked EGFR CAR-T cells with different concentrations of urokinase-type plasminogen activator protease (uPA, R&D Systems) in PBS for 1 hour at room temperature. The cells were then washed with PBS twice and used for subsequent binding and staining experiments.

Intracellular Cytokine Staining.

T cells ($1 \times 10^6$) were co-cultured with target cells at a ratio of 1:1 for 6 hours at 37° C. and 5% $CO_2$ with GolgiPlug (BD Biosciences, San Jose, Calif.) in 96-well round bottom plates. PE-Cy5.5-anti-CD3 antibody, APC-Cy7-anti-CD4 antibody, Pacific blue-CD8 antibody and PE-anti IFN-γ were used for immunostaining. All the antibodies were purchased from BioLegend. Cytofix/Cytoperm Fixation and Permeabilization Kit (BD Biosciences) was used to permeabilize cell membrane and perform intracellular staining according to the manufacturer's instruction.

Specific Cell Lysis Assay.

Lysis of target cells K562-EGFR was measured by comparing survival of target cells K562-EGFR relative to the survival of negative control cells K562. This method has been described previously (Kochenderfer, J N, et al. (2009). Construction and preclinical evaluation of an anti-CD19 chimeric antigen receptor. *J Immunother* 32:689-702). K562 cells were labeled by suspending them in R10 medium with 5 µM fluorescent dye CMTMR (Invitrogen, Carlsbad, Calif.) at a concentration of $1.5 \times 10^6$ cells/mL. The cells were incubated at 37° C. for 30 minutes and then washed twice and suspended in fresh R10 medium. K562-EGFR cells were labeled by suspending them in PBS+0.1% BSA with 5 µM fluorescent dye CFSE at a concentration of $1 \times 10^6$ cells/mL. The cells were incubated 30 minutes at 37° C. After incubation, the same volume of FBS was added into the cell suspension and then incubated for 2 minutes at room temperature. The cells were then washed twice and suspended in fresh R10 medium. Equal number of K562 and K562-EGFR cells ($5 \times 10^4$ each) were combined in the same well for each culture with effector CAR-T cells. Co-cultures were set up in round bottom 96-well plates in triplicate at the following effector-to-target ratios: 1:1, 3:1, and 10:1. The cultures were incubated for 4 hours at 37° C. followed by 7-AAD labeling, according to the manufacturer's instructions (BD Biosciences). Flow cytometric analysis was performed to quantify remaining live (7-AAD-negative) target cells. For each co-culture, the percent survival of K562-EGFR was determined by dividing the percentage of live K562-EGFR by the percentage of live K562 cells. In the wells containing only target and negative control cells without effector cells, the ratio of the percentage of K562-EGFR to the percentage of K562 cells was calculated and used to correct the variation in the starting cell numbers and spontaneous cell death. The cytotoxicity was determined in triplicate and presented in mean±SEM.

For the NCI-H292 and MDA-MB-231 target cells, specific cell lysis was determined as described above, with the following differences. Target cells were labeled with CFSE. Target cells ($5 \times 10^4$) were cultured with effector cells for 18 hours at 37° C. The percentage of survival of target cells was determined by dividing live target cell numbers with effectors over live target cell number without effectors.

Anti-Tumor Efficacy of CAR-T Cells in Non-Small Cell Lung Cancer Xenograft Mouse Model.

The animal experiments were conducted according to the animal protocol approved by USC Institutional Animal Care and Use Committee (IACUC). Six- to eight-week-old female NOD.Cg-Prkdc$^{scid}$IL2Rg$^{tm1Wjl}$/Sz (NSG) mice (Jackson Laboratory, Farmington, Conn.) were used in this study. On day 0, 6×10⁶ NCI-H292 cells, suspended in a total 150 µL of matrigel (Corning, N.Y., N.Y.) diluted 1:1 in RPMI medium, were injected into the right flank of each NSG mouse. When average tumor size reached 120 mm³ on day 12, all the mice were randomized based on the tumor size and assigned into 4 groups (n=8). Mice were treated with 4 million CAR– T cells in 150 µL PBS administered intravenously via tail vein injection twice, on day 13 and day 26, respectively. CAR expression was normalized to 30% in all the CAR groups by addition of donor-matched untransduced T cells. Tumor growth was monitored twice every week. Tumor size was measured by calipers and calculated by the following formula, L×W×H/2. Mice were euthanized when they displayed obvious weight loss, ulceration of tumors, or tumor size larger than 1000 mm³.

Statistical Analysis.

Statistical analysis was performed in GraphPad Prism, version 5.01. One-way ANOVA with Tukey's multiple comparison was performed to assess the differences among different groups in the in vitro assays. Tumor growth curve was analyzed using one-way ANOVA with repeated measures (Sidak's multiple comparison method). Mice survival curve was evaluated by the Kaplan-Meier analysis (log-rank test with Bonferroni corrrection). A P value less than 0.05 was considered statistically significant. Significance of findings was defined as: ns=not significant, P>0.05; *, P<0.05; , P<0.01; *, P<0.001.

Design and Generation of Masked CAR

Given the known anti-apoptotic effects of 4-1BB endodomain and effective cytotoxicity of CD28 endodomain for desired CAR function (van der Stegen, et al (2015). The pharmacology of second-generation chimeric antigen receptors. Nat Rev Drug Discov 14:499-509; Rice, J J, et al (2006). Bacterial display using circularly permuted outer membrane protein OmpX yields high affinity peptide ligands. Protein Science 15:825-836), various forms of the third-generation CAR molecules targeting human EGFR were constructed for this study (FIG. 1a,b). These CARs consisted of a single-chain variable fragment (scFv) derived from the monoclonal antibody cetuximab, the CD8α hinge and transmembrane domain, the CD28 and 4-1BB costimulatory domains, and the CD3ζ T cell receptor signaling domain.

For mCAR, a masking peptide along with a cleavable linker sequence was introduced upstream of the scFv domain, using the amino acid sequences from the probody of cetuximab (Desnoyers, L R, et al. (2013). Tumor-specific activation of an EGFR-targeting probody enhances therapeutic index. Sci Transl Med 5:207ra144). The masking peptide was selected by bacterial display to bind the antigen recognition domain of cetuximab (Rice, J J, et al (2006). Bacterial display using circularly permuted outer membrane protein OmpX yields high affinity peptide ligands. Protein Science 15:825-836), thereby blocking its ability to bind to EGFR. The linker sequence was determined by selection using cellular libraries of peptide substrates (CLiPS) (Boulware, K T, and Daugherty, PS (2006). Protease specificity determination by using cellular libraries of peptide substrates (CLiPS). Proc Natl Acad Sci USA 103:7583-7588) for its responsiveness to multiple tumor-associated proteases, including urokinase-type plasminogen activator (uPA), membrane-type serine protease 1 (MT-SP1/matriptase), and legumain, all of which are upregulated in the tumor microenvironment of many human tumors (Desnoyers, L R, et al. (2013). Tumor-specific activation of an EGFR-targeting probody enhances therapeutic index. Sci Transl Med 5:207ra144). A conventional unmasked CAR without the masking peptide and linker sequence was constructed as a control. We also generated a control CAR construct containing the same masking peptide, but lacking the linker sensitive to protease cleavage, and designated it as NSUB (No protease SUBstrate sequence) CAR. The NSUB CAR has a non-cleavable GS-rich linker instead. All of these CARs were cloned into a retroviral vector for delivery to human T cells.

The engineering of this novel mCAR is based on the integration of a safety switch such that 1) CAR binding sites are blocked by the masking peptide, resulting in quiescent CAR-T cells in systemic circulation or normal tissue environment, but 2) masking peptide is cleaved by proteases locally active in the tumor environment when these CAR-T cells traffic into tumors, thus enabling the activated CAR-T cells to recognize target antigens at the tumor sites.

Attenuated Binding of mCAR to Recombinant EGFR

To test the functional expression of various designed CARs, human peripheral blood mononuclear cells (PBMCs) were stimulated by anti-CD3/CD28 antibodies followed by transduction with retroviral vectors encoding the unmasked, masked, or NSUB form of anti-EGFR CARs. CAR expression was detected using the protein L staining protocol (Zheng, Z L, et al (2012). Protein L: a novel reagent for the detection of Chimeric Antigen Receptor (CAR) expression by flow cytometry. Journal of Translational Medicine 10:29) and analyzed by flow cytometry 8 days post-transduction. A similar level of surface expression of CARs (approximately 30~35% of CAR-positive T cells, FIG. 2a) was detected for all three forms of EGFR CARs, and they were observed to expand similarly under the T cell culture conditions.

To assess the binding capacity of different CAR constructs towards their target antigen EGFR, CAR-T cells were incubated with recombinant human EGFR fused with Fc (designated rhEGFR-Fc) followed by staining with an anti-human IgG Fc antibody. While ~35% of the unmasked CAR-T cells showed binding to EGFR, which corresponded very well to the percentage of CAR-positive cells detected by protein L, the masked and NSUB CAR-T cells exhibited dramatically reduced binding to the target antigen such that only 3% and 0.4% binding were detected, respectively (FIG. 2b). Thus, the masking peptide could effectively block the antigen recognition capability of EGFR CAR-T cells.

mCAR Antigen Binding is Restored by Proteolysis

To explore whether the protease-sensitive linker could be cleaved to expose the binding site and restore CAR binding, CAR-T cells were treated with various concentrations of uPA, a common protease active in a variety of human carcinomas, (Ulisse, S, et al (2009). The urokinase plasminogen activator system: a target for anti-cancer therapy. Current Cancer Drug Targets 9:32-71) before incubation with rhEGFR. As expected, the binding capability of unmasked or NSUB CAR was not markedly different in the presence or absence of uPA treatment (FIG. 3, top and bottom panels). However, the binding of masked CAR to EGFR was largely restored by proteolytic cleavage of the protease-sensitive linker upon uPA treatment. Such protease-mediated binding activation of masked CAR-T cells was found to be dose-dependent; the percentage of masked CAR-T cells that could bind to rhEGFR increased from 6% without uPA treatment to 23% and 29% with the 100 nM and 400 nM of protease, respectively (FIG. 3, middle panel).

Activity of Masked CAR-T Cells was Blocked in the Absence of Protease, but Activated Upon Stimulation with Protease-Secreting Tumor Cells In Vitro Considering that the masking peptide diminished the binding of masked and NSUB CARs to EGFR, we hypothesized that the masking peptide could also prevent the activation of CAR-T cells towards EGFR⁺ cells in the absence of proteases. To test this hypothesis, we generated a target cell line, K562-EGFR, to stably overexpress the human wild-type EGFR. The parental K562 line is a human chronic myeloid leukemia cell line with no EGFR expression (Ghosh, G, et al (2010). Quantifying the sensitivities of EGF receptor (EGFR) tyrosine kinase inhibitors in drug resistant non-small cell lung cancer (NSCLC) cells using hydrogel-based peptide array. *Biosens Bioelectron* 26:424-431) and a very low level of uPA expression (Antonyak, H, et al (2001). Regulation of expression of the components of plasminogen activation system in the leukemic cells. *Exp Oncol* 23: 253-259). We also used two previously studied cancer cell lines, the breast cancer line MDA-MB-231 and lung cancer line NCI-H292, which both have high surface expression of wild-type EGFR (Subik, K, et al. (2010). The expression patterns of ER, PR, HER2, CK5/6, EGFR, Ki-67 and AR by immunohistochemical analysis in breast cancer cell lines. *Breast Cancer* (Auckl) 4:35-41; Raben, D, et al. (2005). The effects of cetuximab alone and in combination with radiation and/or chemotherapy in lung cancer. *Clin Cancer Res* 11:795-805) and high endogenous secretion of tumor-associated proteases, such as uPA and matriptase (Xing, R H, and Rabbani, S A (1999). Transcriptional regulation of urokinase (uPA) gene expression in breast cancer cells: role of DNA methylation. *Int J Cancer* 81:443-450; Ma, Z, et al (2001) Endogenously produced urokinase-type plasminogen activator is a major determinant of the basal level of activated ERK/MAP kinase and prevents apoptosis in MDA-MB-231 breast cancer cells. *J Cell Sci* 114:3387-3396; Liu, G, et al (1995). Co-expression of urokinase, urokinase receptor and PAI-1 is necessary for optimum invasiveness of cultured lung cancer cells. *Int J Cancer* 60:501-506). To test if antigen-specific activation of masked CAR-T cells could be achieved in the protease-active environment, EGFR CAR-T cells were cocultured with K562, K562-EGFR, MDA-MB-231, or NCI-H292 cells. The activation of CAR-T cells was measured by their ability to produce the proinflammatory cytokine interferon γ (IFN-γ) via intracellular cytokine staining (FIG. 4a,b).

In the absence of stimulation or with the stimulation by K562 cells, all of the CAR-T cell groups displayed a background level of IFN-γ secretion. Upon the stimulation of anti-CD3/CD28 antibodies, they all exhibited the same level of IFN-γ secretion for the CD8⁺ CAR-T cells (~20%). As anticipated, unmasked CAR-T cells responded with a similar range of percentages when cocultured with different target cell lines (15.4%, 17.8%, 19.3% for K562-EGFR, MDA-MB-231, NCI-H292, respectively). In contrast, the NSUB CAR-T cells for all tested groups exhibited impaired cytokine response, as compared to unmasked CAR-T cells (1%, 5%, 6% for K562-EGFR, MDA-MB-231, NCI-H292, respectively). Moreover, among the masked EGFR CAR-T cells, only ~0.9% of CD8⁺ cells were capable of secreting IFN-γ in response to stimulation by K562-EGFR cells, which was not significantly different from that of NSUB CAR-T groups. Thus, this finding was consistent with the previous binding data confirming that the activation of CAR-T cells was largely abrogated by the masking peptide for both the masked and NSUB groups. However, upon stimulation by MDA-MB-231 or NCI-H292 tumor cells, which express EGFR and produce tumor-associated proteases, the activation level of masked CAR-T cells (16% and 17.2% CD8⁺IFN-γ⁺, respectively) was largely restored to a level similar to that of the unmasked group. Taken together, these data indicated that the EGFR-specific CAR-T cell function could be selectively activated in a protease-activated environment, but markedly abrogated in the protease-null environment.

We also performed a specific cell lysis assay to test the cytotoxic effect of all groups of CAR-T cells towards the above target cell lines. Similar to the IFN-γ assay, unmasked CAR-T cells lysed all of the target cells, including K562-EGFR, NCI-H292 and MDA-MB-231, whereas masked CAR-T cells only lysed H292 and MDA-MB-231 cells at high effector-to-target ratio and exhibited no killing activity towards K562-EGFR cells (FIG. 5a-c).

Figures 6A, 6B:
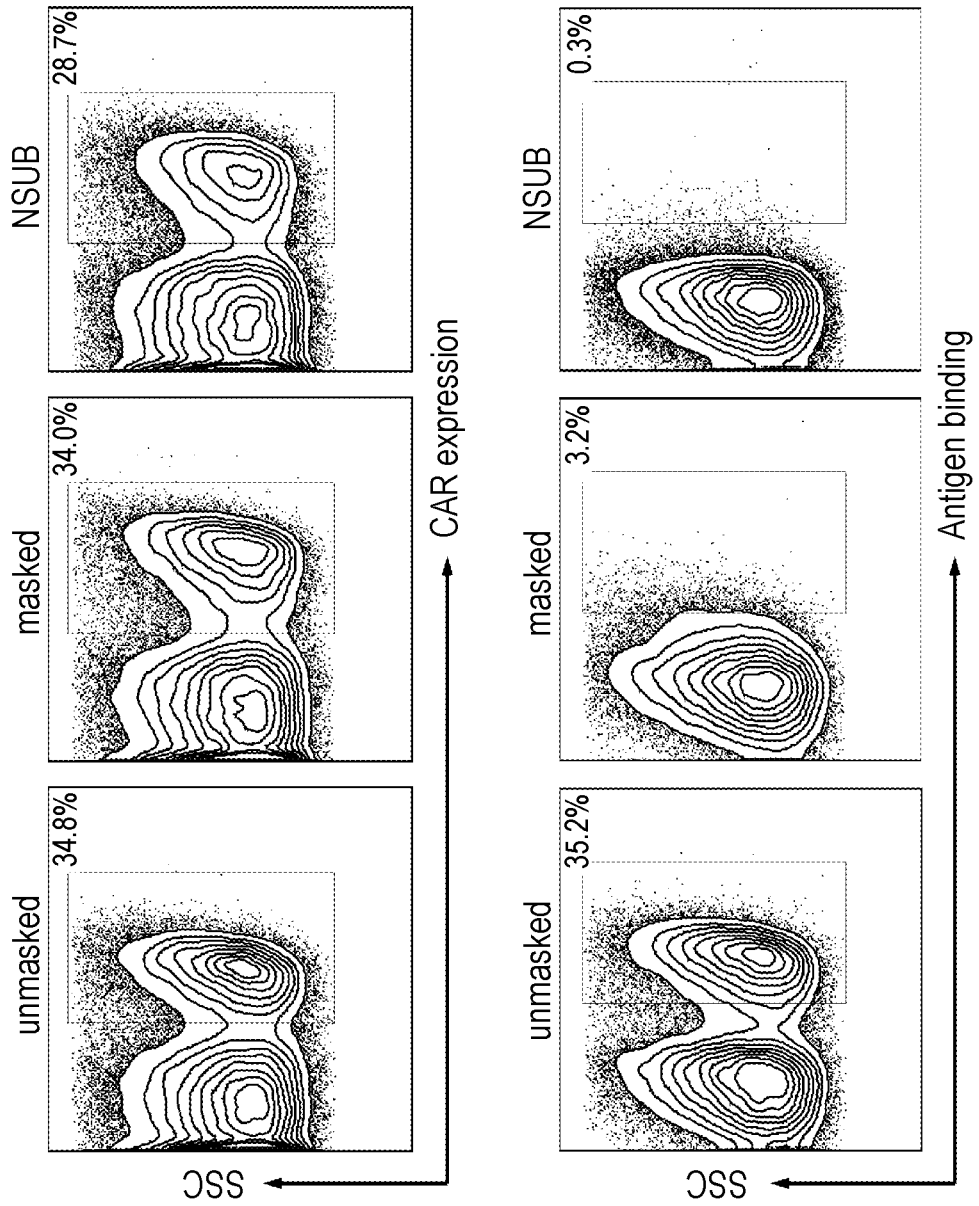
FIG. 6A-FIG. 6B depicts, in accordance with an embodiment of the invention, expression of various CARs in human T cells and their binding capacity to target antigen EGFR. Human PBMCs were activated and transduced with retroviral vectors encoding unmasked, masked, and NSUB anti-EGFR CARs and expanded ex vivo for 10 days.
Figure 7:
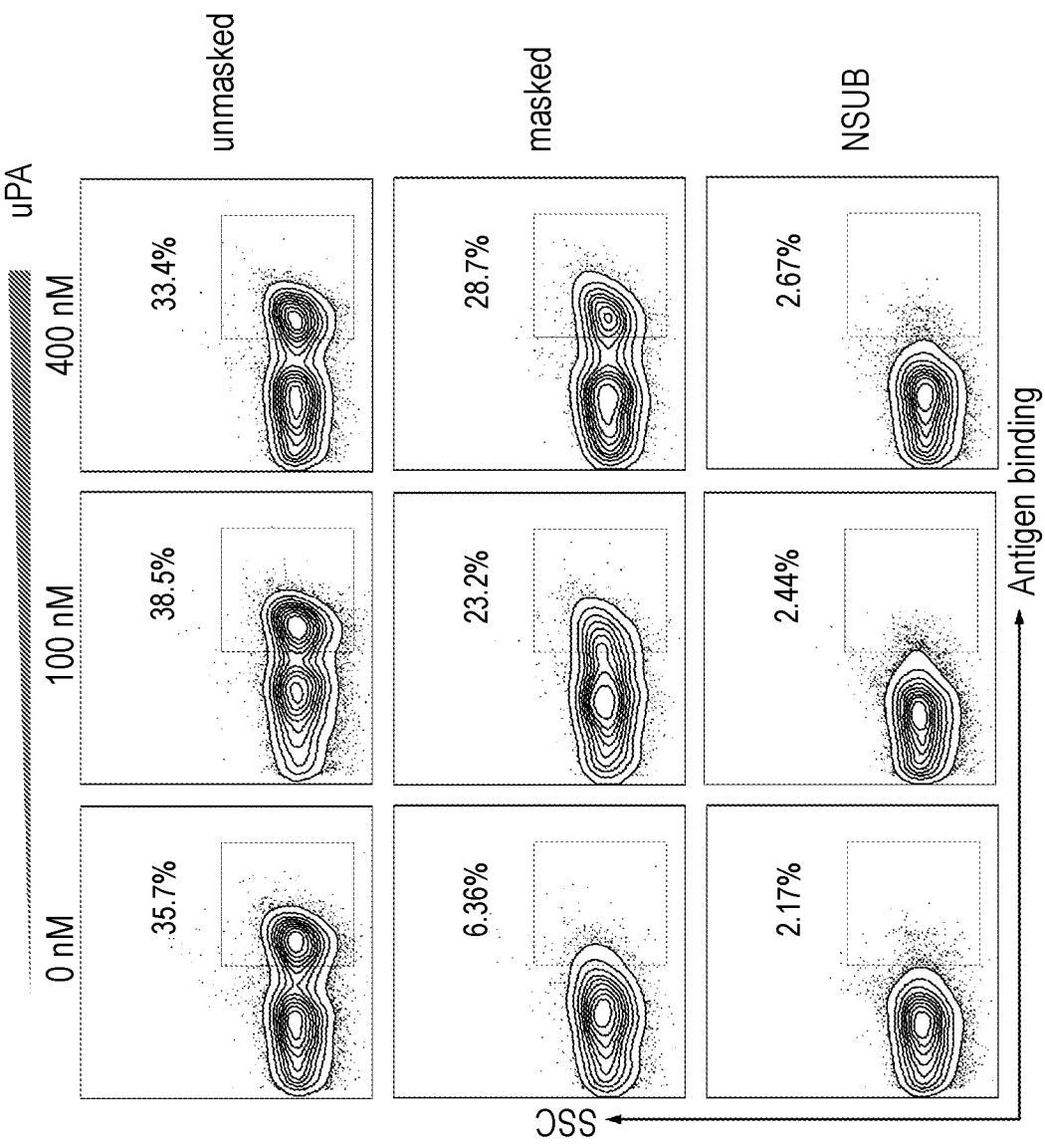
FIG. 7 depicts, in accordance with an embodiment of the invention, binding of various CARs to target antigen EGFR after protease treatment. Unmasked, masked, and NSUB anti-EGFR CAR-T cells were treated with uPA at increasing concentrations (0 nM, 100 nM, and 400 nM) and then stained with recombinant human EGFR-Fc (rhEGFR-Fc) and goat anti-human Fc antibody to assess the effect of protease treatment on CAR binding to antigen.
Figure 8A:
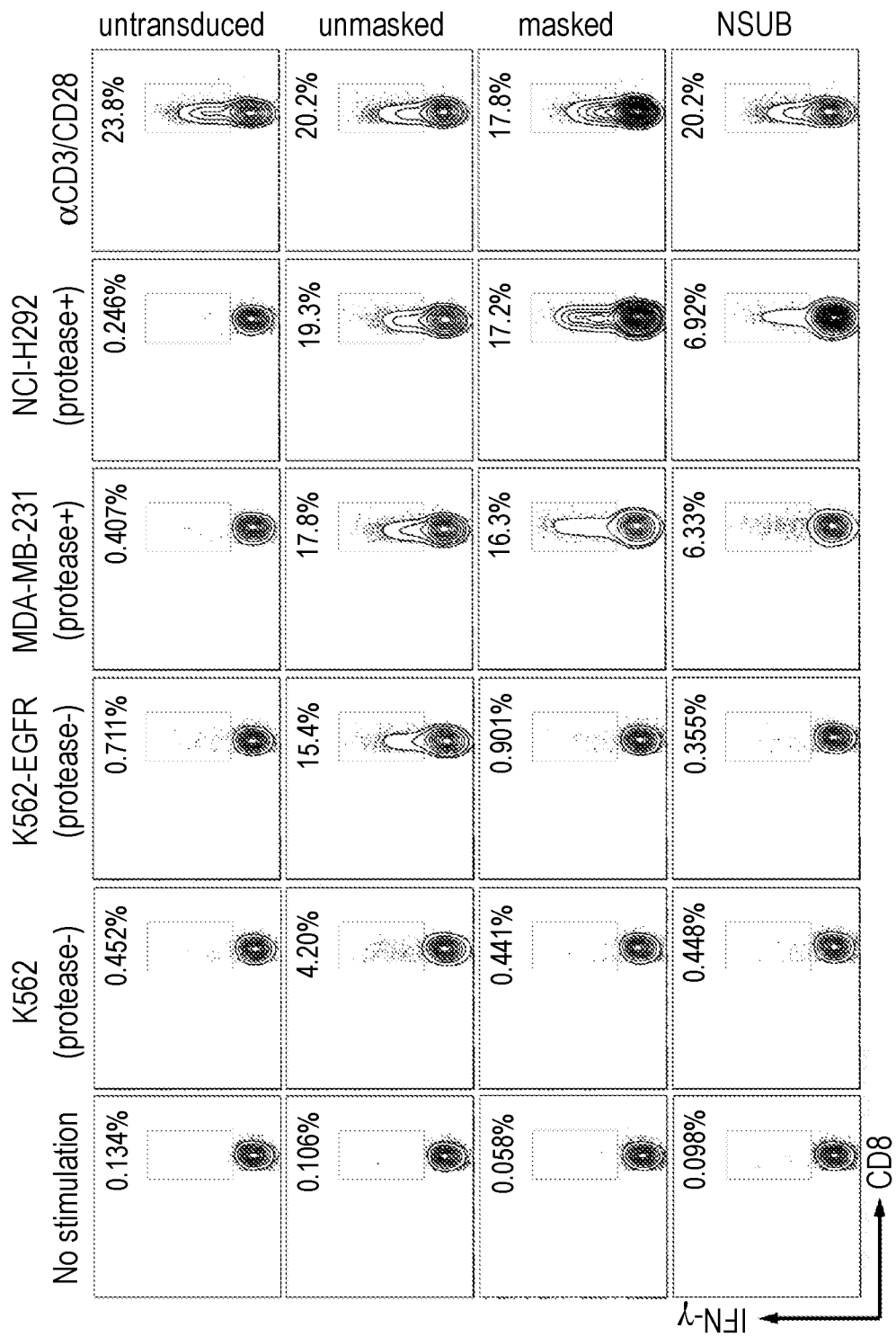
FIG. 8A-FIG. 8B depicts, in accordance with an embodiment of the invention, depicts, in accordance with an embodiment of the invention, intracellular cytokine staining of various CAR-T cells stimulated with different target cells.
Figure 8B:
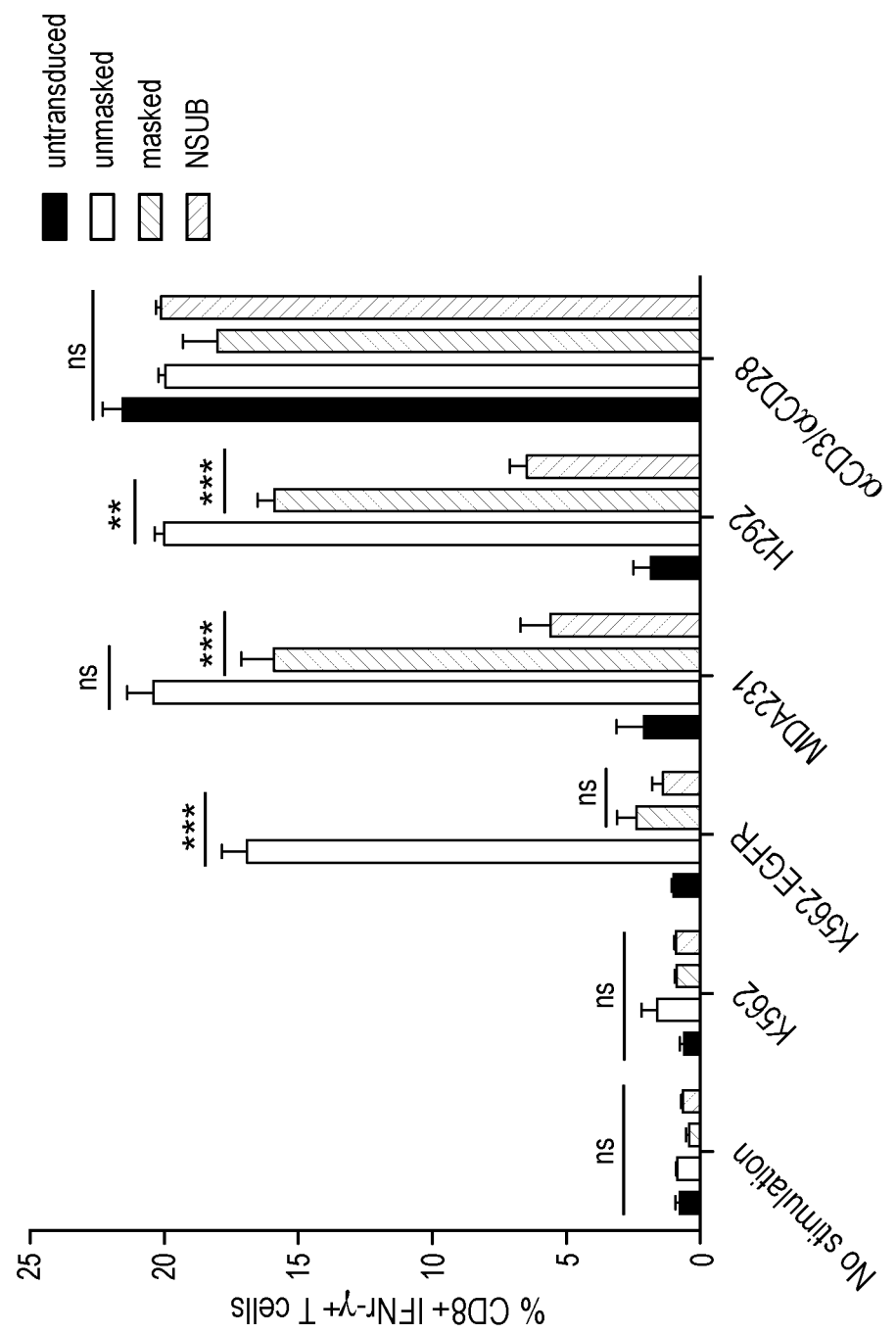

Masked CAR-T Cells Showed Antitumor Efficacy In Vivo Equal to that of Unmasked Cells Having demonstrated the specificity and functionality of masked CAR-T cells in response to tumor cells in vitro, we next sought to investigate their antitumor reactivity in vivo. To evaluate the antitumor efficacy of various CAR-T cells, we utilized a subcutaneous human lung cancer xenograft model in NSG mice (FIG. 6a). NCI-H292 cells (6×10⁶) were injected into the right flank of NSG mice. When the average tumor size reached around 120 mm³ on day 12 after tumor inoculation, all the tumor-bearing mice were randomized into tumor size rank matched cohorts (n=8 per treatment group), and CAR-T treatment was started. Mice were treated with 4 million CAR-T cells through intravenous injection at day 13 and 26, and tumor growth was monitored. Animals in all treatment groups showed tumor progression. Compared with untransduced control T cell group, infusion of NSUB CAR-T cells had no effect on slowing tumor growth (FIG. 6b). However, compared to mice receiving untransduced T cells, those receiving unmasked or masked CAR-T cells resulted in tumor growth inhibition (P=0.0294 for unmasked, P=0.0404 for masked, one-way ANOVA). Consequently, both unmasked and masked CAR-T cells markedly improved the survival of mice (FIG. 6c, P=0.0006 for unmasked, P=0.0036 for masked, log-rank test). Unmasked and masked groups had median survival of 50.5 and 49 days after the first treatment, respectively, compared to untransduced and NSUB groups with median survival of 42 days (FIG. 6c).

"On-target off-tumor" toxicity is a serious limitation for the translational application of CAR-T therapy in solid tumors. This is usually caused by the low level of expression of target antigens in normal tissues. Owing to the high sensitivity of CAR-T cells to target antigens, the on-target toxicity can be especially serious with CAR-based cell therapy compared to conventional antibody therapy. Therefore, target antigens, such as EGFR and HER2 that are overexpressed in various tumors, but also expressed widely in other tissues, are generally considered as "undruggable" targets for CAR-T cells.

Herein, we demonstrate that this limitation can be overcome by re-engineering the CAR molecule into a mCAR via introduction of a cleavable masking peptide to block the antigen recognition site in the scFv domain. Similar to parental unmasked anti-EGFR CAR-T cells, we found that masked anti-EGFR CAR-T cells exhibited similar cytokine production and cell-killing activity towards EGFR-overexpressing breast cancer cell line MDA-MB-231 and lung cancer cell line NCI-H292. Importantly, masked CAR-T cells had markedly reduced reactivity towards EGFR-overexpressing cells secreting little or no protease. In the human lung cancer xenograft model established in NSG mice, the masked CAR-T cells were demonstrated to be as effective as the parental CAR-T cells for inhibiting tumor growth in vivo.

Some efforts have already been made to explore engineering designs to improve the tumor tissue selectivity of CAR-engineered T cells (Klebanoff, C A, et al (2016). Prospects for gene-engineered T cell immunotherapy for solid cancers. *Nat Med* 22:26-36). One elegant strategy exploits dual targeting with two CARs to achieve selective recognition of tumor, but not normal cells. It was demonstrated that T cells expressing two CARs targeting two different antigens could operate as logic gates to control full T cell activation. In one example, two attenuated CARs were designed so that recognition of one antigen target by one CAR could only induce suboptimal T cell activation, while the activation of the second CAR by the second antigen could provide additional costimulatory signal. Thus, activation of both CARs simultaneously resulted in T cells with the full potential to induce antitumor immune response against tumor tissues expressing both antigens (Kloss, C C, et al (2013). Combinatorial antigen recognition with balanced signaling promotes selective tumor eradication by engineered T cells. *Nat Biotechnol* 31:71-75. Alternatively, the same group introduced two functionally different CARs, one inhibitory CAR (iCAR) and another active CAR (aCAR), to the same T cells. When such dual-CAR-T cells encounter the normal tissue environment expressing both antigens, the inhibitory signal triggered by iCAR dominates T cell signaling and preemptively constrains T cell responses. However, when they traffic to the tumor environment with availability of only aCAR, but not iCAR antigen, CAR-T cells can be fully activated to elicit antitumor immunity.[35] Our mCAR method offers one more strategy to create conditionally active CARs for enhancing tumor-specificity of CAR-T cells.

Another method to mitigate the on-target off-tumor toxicity involves tuning the affinity of CAR molecules to better distinguish between antigen targets in tumor tissue and those in normal tissue. Recent work has shown that CARs derived from low-affinity anti-EGFR or anti-HER2 scFv can selectively target tumor cells, while sparing normal tissues with low expression of target antigens (Liu, X, et al. (2015). Affinity-tuned ErbB2 or EGFR chimeric antigen receptor T cells exhibit an increased therapeutic index against tumors in mice. *Cancer Res* 75:3596-3607; Caruso, et al. (2015). Tuning sensitivity of CAR to EGFR density limits recognition of normal tissue while maintaining potent antitumor activity. Cancer Res 75:3505-3518; Chmielewski, M, et al (2004). T cell activation by antibody-like immunoreceptors: increase in affinity of the single-chain fragment domain above threshold does not increase T cell activation against antigen-positive target cells but decreases selectivity. *J Immunol* 173:7647-7653). This approach can be applied in the design of effective and safe CARs, but also has potential drawbacks by the inability to recognize the population of tumor cells with relatively low tumor antigen density. Thus, for tumors with heterogeneous levels of antigen expression, these CAR-engineered cells can eliminate high antigen-expressing tumor cells, but likely miss tumors with low antigen expression. Different from the affinity-tuned design, mCARs can be derived from currently available high-affinity antibodies and the selectivity of mCARs stems from spatially controlled receptor activation. Only in protease-enriched tumor microenvironment do masked CAR-T cells become responsive to targets in the surroundings and trigger downstream cytotoxicity response.

In sum, our study has provided a starting point for further investigation and development of the masked CAR platform. However, although we observed enhanced selectivity between target cells with or without tumor-associated proteases in vitro and antitumor reactivity in the animal study, the safety and efficacy of the mCAR construct in humans still requires further evaluation and examination in preclinical trials involving nonhuman privates or a phase I pilot trial. Our CARs are derived from ceutximab, which has minimal cross-reactivity with mouse EGFR, and therefore it is difficult to evaluate the reactivity of masked anti-EGFR CAR-T cells against normal tissues in a mouse model. Also, in this study, CAR-T was administered as a single agent, typically having only barely satisfactory antitumor efficacy, especially in solid tumors. In a clinical setting, combination therapies including both CAR-T therapy and chemotherapy or immune checkpoint inhibitors, can be used to enhance treatment efficacy. In addition, it has been tested before[20] that the protease-cleavable linker used in our mCAR design is sensitive to multiple proteases that are locally active in tumor microenvironment, but not to proteases in normal tissues, such as tissue plasminogen activator (tPA), plasmin and KLK5. However, the evaluation of an even broader range of normal proteases is desirable before clinical investigation in humans.

Since EGFR is dysregulated in many kinds of human carcinomas, this study offers a pathway toward the design of CARs capable of targeting different types of cancers. This masked CAR strategy may help expand the applicability of CAR-T cells to cancers lacking otherwise "druggable" tumor antigens. It also potentially enables CAR-T therapy to target tumor antigens such as carbonic anhydrase IX or HER2, in which the "on-target off-tumor" side effect was shown to be intolerable and life-threatening (Morgan, R A, et al (2010). Case report of a serious adverse event following the administration of T cells transduced with a chimeric antigen receptor recognizing ERBB2. *Mol Ther* 18: 843-851; Lamers, C H, et al. (2013). Treatment of metastatic renal cell carcinoma with CAIX CAR-engineered T cells: clinical evaluation and management of on-target toxicity. *Mol Ther* 21:904-912).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A masked chimeric antigen receptor (mCAR), comprising:
   a. a masking peptide;
   b. antigen-specific targeting domain;
   c. a transmembrane domain;
   d. at least one co-stimulatory domain; and
   e. an intracellular signaling domain,
   wherein the antigen-specific targeting domain comprises an antigen-specific single-chain variable fragment (scFv),
   wherein the masking peptide comprises a mask that specifically binds the antigen-specific targeting domain and a cleavage site, and
   wherein when the mask is cleaved, the mCAR is active and can bind the antigen; and
   when the mask is uncleaved, the mCAR is inactive and its ability to bind the antigen is reduced compared to when the masked is cleaved or compared to an unmasked chimeric antigen receptor that is otherwise identical to the mCAR except without the masking peptide,
   wherein the antigen-specific scFv comprises:
   (i)
   the variable light chain of trastuzumab and the variable heavy chain of trastuzumab, wherein the mask of the masking peptide comprises a polypeptide sequence that is 100% or or 95% about 99%, 98%, 97%, 96% or 95% identical to the polypeptide sequence set forth in SEQ ID NO: 17; or (ii) a bivalent scFv, said bivalent scFv comprises a variable light chain whose sequence is 100% or about 99%, 98%, 97%, 96% or 95% identical to SEQ ID NO:3, a variable heavy chain whose sequence is 100% or about 99%, 98%, 97%, 96% or 95% identical to SEQ ID NO:4, the variable light chain of trastuzumab, and the variable heavy chain of trastuzumab, wherein the mask of the masking peptide comprises the polypeptide sequence set forth in SEQ ID NO: 1 and the polypeptide sequence set forth in SEQ ID NO: 17.

2. The mCAR of claim 1, further comprising an extracellular spacer domain.

3. The mCAR of claim 1, wherein the mask and the cleavage site are linked by a linker.

4. The mCAR of claim 1, wherein the masking peptide is linked to a chimeric antigen receptor (CAR) by a linker, wherein the CAR comprises the antigen-specific targeting domain, the transmembrane domain, the at least one co-stimulatory domain, and the intracellular signaling domain.

5. The mCAR of claim 1, wherein the cleavage site is a protease specific cleavage site.

6. The mCAR of claim 3, wherein the mCAR in an uncleaved state comprises a structural arrangement from N-terminus to C-terminus as follows: mask-linker-cleavage site-antigen specific targeting domain-transmembrane domain-costimulatory domain-intracellular signaling domain.

7. The mCAR of claim 3, further comprising an extracellular spacer domain, wherein the mCAR in an uncleaved state comprises a structural arrangement from N-terminus to C-terminus as follows: mask-linker-cleavage site-antigen specific targeting domain-extracellular spacer domain-transmembrane domain-costimulatory domain-intracellular signaling domain.

8. The mCAR of claim 2, wherein the extracellular spacer domain comprises an Fc fragment of an antibody, a hinge region of an antibody, a CH2 region of an antibody, a CH3 region of an antibody, an artificial spacer sequence or combinations thereof.

9. The mCAR of claim 8, wherein the extracellular spacer domain comprises (i) a hinge, CH2 and CH3 region of IgG4, (ii) a hinge region of IgG4, (iii) a hinge and CH2 region of IgG4, (iv) a hinge region of CD8a, (v) a hinge, CH2 and CH3 region of IgG1, (vi) a hinge region of IgG1, (vi) a hinge and CH2 region of IgG1, or (vii) combinations thereof.

10. The mCAR of claim 1, wherein the transmembrane domain comprises a transmembrane region of a Type I transmembrane protein, an artificial hydrophobic sequence, or combinations thereof.

11. The mCAR of claim 10, wherein the transmembrane domain comprises a transmembrane domain of a zeta chain of a T cell receptor complex, CD28, CD8α, or combinations thereof.

12. The mCAR of claim 1, wherein the co-stimulatory domain comprises a signaling domain from CD28, CD137 (4-1BB), CD134 (OX40), Dap10, CD27, CD2, CD5, ICAM-1, LFA-1, Lck, TNFR-I, TNFR-II, Fas, CD30, CD40 or combinations thereof.

13. The mCAR of claim 1, wherein the intracellular signaling domain comprises a signaling domain of a human CD3 zeta chain, FcγRIII, FcεRI, a cytoplasmic tail of a Fc receptor, an immunoreceptor tyrosine-based activation motif (ITAM) bearing cytoplasmic receptors, or combinations thereof.

14. A masked chimeric antigen receptor (mCAR) comprising the sequence set forth in SEQ ID NO: 29.

15. A method for treating cancer in a subject in need thereof, comprising:
administering a therapeutically effective amount of a composition comprising genetically modified T-cells or natural killer (NK)-cells comprising a masked chimeric antigen receptor (mCAR) to the subject, so as to treat the cancer, wherein the antigen-specific targeting domain is associated with the cancer,
wherein the mCAR comprises
a. a masking peptide;
b. antigen-specific targeting domain;
c. a transmembrane domain;
d. at least one co-stimulatory domain; and
e. an intracellular signaling domain,
wherein the antigen-specific targeting domain comprises an antigen-specific single-chain variable fragment (scFv),
wherein the masking peptide comprises a mask that specifically binds the antigen-specific targeting domain and a cleavage site,
wherein the antigen-specific scFv comprises the variable light chain of trastuzumab and the variable heavy chain of trastuzumab, wherein the mask of the masking peptide comprises a polypeptide sequence set forth in SEQ ID NO:17.

16. The method of claim 15, wherein the cancer is lung cancer, breast cancer, kidney cancer or neuroblastoma.

17. The mCAR of claim 1, wherein the mask of the masking peptide comprises a sequence set forth in SEQ ID NO: 17; and the cleavage site of the masking peptide comprises one or more sequences set forth in SEQ ID NOs: 5-7, 2 and 26-28.

18. A composition comprising genetically engineered cells comprising the mCAR of claim 1.

19. The composition of claim 18, wherein the genetically engineered cells are T-lymphocytes (T-cells), naive T cells ($T_N$), memory T cells, natural killer cells, hematopoietic stem cells, hematopoietic stem cells, or pluripotent stem cells.

20. A composition comprising genetically engineered cells comprising the mCAR of claim 14.

* * * * *

SEQUENCE LISTING

```
<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: synthetic

<400> SEQUENCE: 1

Cys Ile Ser Pro Arg Gly Cys Pro Asp Gly Pro Tyr Val Met Tyr
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Leu Ser Gly Arg Ser Asp Asn His
1               5
```

<210> SEQ ID NO 3
<211> LENGTH: 108
<212> TYPE: PRT
<213> ORGANISM: Artificial Sequence
<220> FEATURE:
<223> OTHER INFORMATION: synthetic

<400> SEQUENCE: 3

Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 4
<211> LENGTH: 119
<212> TYPE: PRT
<213> ORGANISM: Artificial Sequence
<220> FEATURE:
<223> OTHER INFORMATION: synthetic

<400> SEQUENCE: 4

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ser
        115

<210> SEQ ID NO 5
<211> LENGTH: 6
<212> TYPE: PRT
<213> ORGANISM: Artificial Sequence
<220> FEATURE:
<223> OTHER INFORMATION: synthetic

<400> SEQUENCE: 5

Cys His Tyr Ser Glu Leu
1               5

<210> SEQ ID NO 6

```
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Asp Val Glu Xaa Asn Pro Gly Pro
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

Asp Ile Glu Xaa Asn Pro Gly Pro
1               5

<210> SEQ ID NO 8
<211> LENGTH: 21
<212> TYPE: PRT
<213> ORGANISM: Artificial Sequence
<220> FEATURE:
<223> OTHER INFORMATION: synthetic

<400> SEQUENCE: 8

Gln Gly Gln Ser Gly Gln Cys Ile Ser Pro Arg Gly Cys Pro Asp Gly
1               5                   10                  15

Pro Tyr Val Met Tyr
            20

<210> SEQ ID NO 9
<211> LENGTH: 13
<212> TYPE: PRT
<213> ORGANISM: Artificial Sequence
<220> FEATURE:
<223> OTHER INFORMATION: synthetic

<400> SEQUENCE: 9

Leu Ser Gly Arg Ser Asp Asn His Gly Ser Ser Gly Thr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: synthetic

<400> SEQUENCE: 10

Gly Ser Ser Gly Gly Ser Gly Gly Ser Gly Gly Ser Gly
1               5                   10

<210> SEQ ID NO 11
<211> LENGTH: 5
<212> TYPE: PRT
<213> ORGANISM: Artificial Sequence
```

```
<220> FEATURE:
<223> OTHER INFORMATION: synthetic

<400> SEQUENCE: 11

Gly Ser Ser Gly Thr
1               5

<210> SEQ ID NO 12
<211> LENGTH: 47
<212> TYPE: PRT
<213> ORGANISM: Artificial Sequence
<220> FEATURE:
<223> OTHER INFORMATION: synthetic

<400> SEQUENCE: 12

Gln Gly Gln Ser Gly Gln Cys Ile Ser Pro Arg Gly Cys Pro Asp Gly
1               5                   10                  15

Pro Tyr Val Met Tyr Gly Ser Ser Gly Ser Gly Ser Gly Ser Gly Gly
                20                  25                  30

Ser Gly Leu Ser Gly Arg Ser Asp Asn His Gly Ser Ser Gly Thr
            35                  40                  45

<210> SEQ ID NO 13
<211> LENGTH: 46
<212> TYPE: PRT
<213> ORGANISM: Artificial Sequence
<220> FEATURE:
<223> OTHER INFORMATION: synthetic

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 14
<211> LENGTH: 68
<212> TYPE: PRT
<213> ORGANISM: Artificial Sequence
<220> FEATURE:
<223> OTHER INFORMATION: synthetic

<400> SEQUENCE: 14

Phe Trp Val Leu Val Val Val Gly Gly Val Leu Ala Cys Tyr Ser Leu
1               5                   10                  15

Leu Val Tyr Val Ala Phe Ile Ile Phe Trp Val Arg Ser Lys Arg Ser
                20                  25                  30

Arg Gly Gly His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser
65

<210> SEQ ID NO 15
<211> LENGTH: 47
<212> TYPE: PRT
<213> ORGANISM: Artificial Sequence
<220> FEATURE:
<223> OTHER INFORMATION: synthetic
```

<400> SEQUENCE: 15

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 16
<211> LENGTH: 112
<212> TYPE: PRT
<213> ORGANISM: Artificial Sequence
<220> FEATURE:
<223> OTHER INFORMATION: synthetic

<400> SEQUENCE: 16

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 17
<211> LENGTH: 12
<212> TYPE: PRT
<213> ORGANISM: Artificial Sequence
<220> FEATURE:
<223> OTHER INFORMATION: synthetic

<400> SEQUENCE: 17

Leu Leu Gly Pro Tyr Glu Leu Trp Glu Leu Ser His
1               5                   10

<210> SEQ ID NO 18
<211> LENGTH: 36
<212> TYPE: DNA
<213> ORGANISM: Artificial Sequence
<220> FEATURE:
<223> OTHER INFORMATION: synthetic

<400> SEQUENCE: 18
tatgaattcg ccaccatggt attgctgcct gggtcc                             36

<210> SEQ ID NO 19
<211> LENGTH: 36
<212> TYPE: DNA
<213> ORGANISM: Artificial Sequence
<220> FEATURE:
<223> OTHER INFORMATION: synthetic

<400> SEQUENCE: 19
gcggaattct taaaggttac cttcgttctc tagggc                             36

<210> SEQ ID NO 20
<211> LENGTH: 63
<212> TYPE: DNA
<213> ORGANISM: Artificial Sequence
<220> FEATURE:
<223> OTHER INFORMATION: synthetic

<400> SEQUENCE: 20
tatgtcgaca tgcgaccctc cgggacggcg gaattcttaa aggttacctt cgttctctag    60
ggc                                                                  63

<210> SEQ ID NO 21
<211> LENGTH: 34
<212> TYPE: DNA
<213> ORGANISM: Artificial Sequence
<220> FEATURE:
<223> OTHER INFORMATION: synthetic

<400> SEQUENCE: 21
tcgtctagac cttcactgtg tctgcaaatc tgcc                                34

<210> SEQ ID NO 22
<211> LENGTH: 17
<212> TYPE: PRT
<213> ORGANISM: Artificial Sequence
<220> FEATURE:
<223> OTHER INFORMATION: synthetic

<400> SEQUENCE: 22

Arg Cys Asn Pro Asn Met Glu Pro Pro Arg Cys Trp Ala Ala Glu Gly
1               5                   10                  15

Asp

<210> SEQ ID NO 23
<211> LENGTH: 17
<212> TYPE: PRT
<213> ORGANISM: Artificial Sequence
<220> FEATURE:
<223> OTHER INFORMATION: synthetic

<400> SEQUENCE: 23

Val Cys Asn Pro Leu Thr Gly Ala Leu Leu Cys Ser Ala Ala Glu Gly
1               5                   10                  15

Asp

<210> SEQ ID NO 24
<211> LENGTH: 8
<212> TYPE: PRT
<213> ORGANISM: Artificial Sequence
<220> FEATURE:
<223> OTHER INFORMATION: synthetic

<400> SEQUENCE: 24

Leu Ser Thr Ala Phe Ala Arg Val
1               5

<210> SEQ ID NO 25
<211> LENGTH: 11
<212> TYPE: PRT
<213> ORGANISM: Artificial Sequence
<220> FEATURE:
<223> OTHER INFORMATION: synthetic

<400> SEQUENCE: 25

```
<210> SEQ ID NO 26
<211> LENGTH: 10
<212> TYPE: PRT
<213> ORGANISM: Artificial Sequence
<220> FEATURE:
<223> OTHER INFORMATION: synthetic

<400> SEQUENCE: 26

Val Leu Val Pro Met Ala Met Met Ala Ser
1               5                   10

<210> SEQ ID NO 27
<211> LENGTH: 8
<212> TYPE: PRT
<213> ORGANISM: Artificial Sequence
<220> FEATURE:
<223> OTHER INFORMATION: synthetic

<400> SEQUENCE: 27

Gly Pro Leu Gly Ile Ala Gly Gln
1               5

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Pro Val Gly Leu Ile Gly
1               5

<210> SEQ ID NO 29
<211> LENGTH: 556
<212> TYPE: PRT
<213> ORGANISM: Artificial Sequence
<220> FEATURE:
<223> OTHER INFORMATION: synthetic

<400> SEQUENCE: 29
```

Ala Leu Gly Pro Gly Arg Glu Tyr Arg Ala Leu
1               5                   10

Gln Gly Gln Ser Gly Gln Cys Ile Ser Pro Arg Gly Cys Pro Asp Gly
1               5                   10                  15

Pro Tyr Val Met Tyr Gly Ser Ser Gly Ser Gly Ser Gly Gly
                20                  25                  30

Ser Gly Leu Ser Gly Arg Ser Asp Asn His Ile Leu Leu Thr Gln Ser
            35                  40                  45

Pro Val Ile Leu Ser Val Ser Pro Gly Glu Arg Val Ser Phe Ser Cys
        50                  55                  60

Arg Ala Ser Gln Ser Ile Gly Thr Asn Ile His Trp Tyr Gln Gln Arg
65                  70                  75                  80

Thr Asn Gly Ser Pro Arg Leu Leu Ile Lys Tyr Ala Ser Glu Ser Ile
                85                  90                  95

Ser Gly Ile Pro Ser Arg Phe Ser Gly Ser Gly Ser Gly Thr Asp Phe
            100                 105                 110

Thr Leu Ser Ile Asn Ser Val Glu Ser Glu Asp Ile Ala Asp Tyr Tyr
        115                 120                 125

Cys Gln Gln Asn Asn Asn Trp Pro Thr Thr Phe Gly Ala Gly Thr Lys
130                 135                 140

Leu Glu Leu Lys Arg Gly Gly Gly Ser Gly Gly Gly Ser Gly
145                 150                 155                 160

Gly Gly Gly Ser Gln Val Gln Leu Lys Gln Ser Gly Pro Gly Leu Val
            165                 170                 175

Gln Pro Ser Gln Ser Leu Ser Ile Thr Cys Thr Val Ser Gly Phe Ser
            180                 185                 190

Leu Thr Asn Tyr Gly Val His Trp Val Arg Gln Ser Pro Gly Lys Gly
        195                 200                 205

Leu Glu Trp Leu Gly Val Ile Trp Ser Gly Gly Asn Thr Asp Tyr Asn
    210                 215                 220

Thr Pro Phe Thr Ser Arg Leu Ser Ile Asn Lys Asp Asn Ser Lys Ser
225                 230                 235                 240

Gln Val Phe Phe Lys Met Asn Ser Leu Gln Ser Asn Asp Thr Ala Ile
            245                 250                 255

Tyr Tyr Cys Ala Arg Ala Leu Thr Tyr Tyr Asp Tyr Glu Phe Ala Tyr
        260                 265                 270

Trp Gly Gln Gly Thr Leu Val Thr Val Ser Ser Thr Thr Thr Pro Ala
    275                 280                 285

Pro Arg Pro Pro Thr Pro Ala Pro Thr Ile Ala Ser Gln Pro Leu Ser
290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Phe Trp Val Leu Val Val Val
            325                 330                 335

Gly Gly Val Leu Ala Cys Tyr Ser Leu Leu Val Tyr Val Ala Phe Ile
        340                 345                 350

Ile Phe Trp Val Arg Ser Lys Arg Ser Arg Gly Gly His Ser Asp Tyr
    355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Arg Phe Ser
385                 390                 395                 400

Val Val Lys Arg Gly Arg Lys Lys Leu Leu Tyr Ile Phe Lys Gln Pro
            405                 410                 415

Phe Met Arg Pro Val Gln Thr Thr Gln Glu Glu Asp Gly Cys Ser Cys
        420                 425                 430

Arg Phe Pro Glu Glu Glu Glu Gly Gly Cys Glu Leu Arg Val Lys Phe
    435                 440                 445

Ser Arg Ser Ala Asp Ala Pro Ala Tyr Gln Gln Gly Gln Asn Gln Leu
450                 455                 460

Tyr Asn Glu Leu Asn Leu Gly Arg Arg Glu Glu Tyr Asp Val Leu Asp
465                 470                 475                 480

Lys Arg Arg Gly Arg Asp Pro Glu Met Gly Gly Lys Pro Arg Arg Lys
            485                 490                 495

Asn Pro Gln Glu Gly Leu Tyr Asn Glu Leu Gln Lys Asp Lys Met Ala
        500                 505                 510

Glu Ala Tyr Ser Glu Ile Gly Met Lys Gly Glu Arg Arg Arg Gly Lys
    515                 520                 525

Gly His Asp Gly Leu Tyr Gln Gly Leu Ser Thr Ala Thr Lys Asp Thr
    530                 535                 540

Tyr Asp Ala Leu His Met Gln Ala Leu Pro Pro Arg
545                 550                 555

```
<210> SEQ ID NO 30
<211> LENGTH: 32
<212> TYPE: DNA
<213> ORGANISM: Artificial Sequence
<220> FEATURE:
<223> OTHER INFORMATION: synthetic

<400> SEQUENCE: 30
ttacgcggcc gcgccaccat ggctctgcct gt                                     32

<210> SEQ ID NO 31
<211> LENGTH: 31
<212> TYPE: DNA
<213> ORGANISM: Artificial Sequence
<220> FEATURE:
<223> OTHER INFORMATION: synthetic

<400> SEQUENCE: 31
ttagaattct catcttggtg gcagagcctg c                                      31

<210> SEQ ID NO 32
<211> LENGTH: 47
<212> TYPE: PRT
<213> ORGANISM: Artificial Sequence
<220> FEATURE:
<223> OTHER INFORMATION: synthetic construct

<400> SEQUENCE: 32

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Gly Gly Ser Gly Gly Gly Ser Gly Gly Ser Ser Gly Thr
        35                  40                  45
```